United States Patent
Song et al.

(10) Patent No.: US 6,423,499 B1
(45) Date of Patent: Jul. 23, 2002

(54) PCR PRIMERS FOR DETECTION AND IDENTIFICATION OF PLANT PATHOGENIC SPECIES, SUBSPECIES, AND STRAINS OF ACIDOVORAX

(75) Inventors: Wan-Yeob Song; Hyung-Moo Kim, both of Chonbuk (KR); Norman W. Schaad, Meyersville, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 4 days.

(21) Appl. No.: 09/703,807

(22) Filed: Nov. 2, 2000

Related U.S. Application Data

(63) Continuation-in-part of application No. 09/393,877, filed on Sep. 10, 1999, now Pat. No. 6,146,834.

(51) Int. Cl.$^7$ .................................................. C12Q 1/68
(52) U.S. Cl. .................. 435/6; 435/4; 435/5; 435/91.1; 435/91.2; 435/69.1
(58) Field of Search .......................... 435/4, 5, 6, 91.1, 435/91.2, 69.1

(56) References Cited

U.S. PATENT DOCUMENTS

| | | | |
|---|---|---|---|
| 5,472,871 A | * 12/1995 | Wood et al. | 435/252.3 |
| 5,576,184 A | * 11/1996 | Better et al. | 435/7.23 |
| 5,679,635 A | * 10/1997 | Matalon et al. | 435/6 |
| 5,763,214 A | * 6/1998 | Hu et al. | 435/69.1 |

OTHER PUBLICATIONS

Gurtler, Volker et al., "Typing of *Staphylococcus aureus* Strains by PCR–Amplification of Variable–Length 16s–23s rDNA Spacer Regions: Characterization of Spacer Sequences", *Microbiology*, vol. 141, pp. 1255–1265, 1995.
Harvey,Steve et al., "Loss of the Spacer Loop Sequence from the rrnB Operon in the *Escherichia coli* K–12 Subline That Bears the relA1 Mutation", *J. Bacteriology*, vol. 170(3), pp. 1235–1238, Mar., 1988.
Islam, Dilara et al., "Detection of *Shigella dysenteriae* Type 1 and *Shigella flexneri* in Feces by Immunomagnetic Isolation and Polymerase Chain Reaction", *J. Clinical Microbiology*, vol. 30(11), pp. 2801–2806, Nov., 1992.
Judd, Adam K., et al., "Use of Repetitive Sequences and the Polymerase Chain Reaction Technique to Classify Genetically Related *Bradyrhizobium japonicum* Serocluster 123 Strains", *Applied Environmental Microbiology*, vol. 59(6), pp. 1702–1707, Jun., 1993.
Katz, Jonathan B., et al., "Colorimetric Diagnosis of Prolonged Bluetongue Viremia in Sheep, Using An Enzyme–Linked Oligonucleotide Sorbent Assay of Amplified Viral Nucleic Acids", *Am. J. Vet. Res.*, vol. 54(12), pp. 2021–2026, Dec., 1993.
Loughney, Kate et al., "RNA Genes are Found Between the 16S and 23S rRNA Genes in *Bacillus subtilis*", *Nuc. Acids Res.*, vol. 10(5), pp. 1607–1624, 1982.
Luneberg, Edeltraud et al., "Detection of *Mycoplasma pneumoniae* by Polymerase Chain Reaction and Nonradioactive Hybridization in Microtiter Plates", *J. ClinicalMicrobiology*, vol. 31(5), pp. 1088–1094, May, 1993.
Prosen, D., et al., "Specific Detection of *Pseudomonas syringae* pv. phaseolicola DNA in Bean Seed by Polymerase Chain Reaction–Based Amplification of a Phaseolotoxin Gene Region", *Phytopathology*, vol. 83(9), pp. 965–970, 1993.
Schaad, Norman W., et al., "*Pseudomonas pseudoalcaligenes* subsp. citrulli subsp. nov.", *Int. J. Syst. Bacteriol.*, vol. 28(1), pp. 117–125, Jan., 1978.

(List continued on next page.)

*Primary Examiner*—W. Gary Jones
*Assistant Examiner*—Janell E. Taylor
(74) *Attorney, Agent, or Firm*—M. Howard Silverstein; John D. Fado; Evelyn M. Rabin

(57) ABSTRACT

We sequenced a 619 and 617 bp fragment of the inner spacer region of 16S–23S rDNA of a strain of *Acidovorax avenae* representing pathogens from several hosts, including foxtail, oats, corn, rice, millet, sugarcane, orchid, and watermelon and a strain of *A. avenae* subsp. *citrulli* pathogenic only to watermelon and melons, respectively, for the purpose of designing PCR primers for their identification. These plant pathogens were previously considered as non-fluorescent pseudomonads and have been recently reclassified as *Acidovorax avenae* subsp. avenae, *A. avenae* subsp. *cattleyae*, and *A. avenae* subsp. *citrulli*. Several sets of primers were designed. Primers identified by SEQ ID NO:1 and SEQ ID NO:2 of *A. avenae* subsp. *avenae* reacted with all strains of *A. avenae* subsp. *avenae* (previously named *P. avenae* or *P. alboprecipitans*) originating from foxtail, oats, corn, rice, sugarcane, and millet, *A. avenae* subsp. *cattleyae* (previously named *P. pseudoalcaligenes* subsp. *cattleyae*) from orchid, and *A. avenae* subsp. *citrulli* (previously named *P. pseudoalcaligenes* subsp. *citrulli*) from watermelon and melon. Primers identified by SEQ ID NO:3, SEQ ID NO:4, SEQ ID NO:5, and SEQ ID NO:6 of subsp. *citrulli* reacted with all strains of *A. avenae* subsp. *citrulli*, but not with any other strain of *A. avenae* subsp. *avenae*. Primers identified by SEQ ID NO:10, SEQ ID NO:11, and SEQ ID NO:12, reacted with the rice strains of *A. avenae* subsp. *avenae*, but not with any other strain of *A. avenae* subsp. *avenae* or any other subspecies of *A. avenae*. None of fifty-three other bacteria tested reacted with these sets of primers. The citrulli-specific primers and rice strain-specific primers should prove especially useful for the specific, sensitive, and rapid detection of these serious seedborne pathogens in watermelon and rice seeds, respectively.

19 Claims, 7 Drawing Sheets

OTHER PUBLICATIONS

Schaad, Norman W., et al., "A Combined Biological and Enzymatic Amplification (BIO–PCR) Technique to Detect *Pseudomonas syringae* pv. phaseolicola in Bean Seed Extracts", *Phytopathology*, vol. 85(2), pp. 243–248, 1995.

Welsh, John et al., "Fingerprinting Genomes Using PCR with Arbitrary Primers", *Nucleic Acids Res.*, vol. 18(24), pp. 7213–7218, 1990.

Willems, A., et al., "Transfer of Several Phytopathogenic Pseudomonas Species to Acidovorax as *Acidovorax avenae* subsp. avenae subsp. nov., comb. nov., *Acidovorax avenae* subsp. citrulli, *Acidovorax avenae* subsp. cattleyae, and *Acidovorax konjaci*", *Int. J. Syst. Bacteriol.*, vol. 42(1), pp. 107–119, Jan., 1992.

Zavaleta, Amparo I., et al., "16S–23S rDNA Intergenic Sequences Indicate that *Leuconostoc oenos* is Phylogenetically Homogeneous", *Microbiology*, vol. 142, pp. 2105–2114, 1996.

Minsavage, G.V., et al., "Detection of the Watermelon Fruit Blotch Pathogen on Seeds with the Polymerase Chain Reaction", *Ann. Mtg. Amer. Phytopathology*, Abstract 379, 1995.

Zeigler, R.S., et al., "Differential Culture Medium for Pseudomonas Species Causing Sheath Rot (ShR) and Grain Discoloration (GID) of Rice", *Intl. Rice Res. Newsletter*, vol. 14(1), pp. 27–28, 1989.

Song, W.Y, et al., "Development of PCR Primers for Detection of *Pseudomonas avenae*", *Phytopathology*, vol. 87(6), p. 92, 1997.

Kim, H.M., et al., "Characterization of Ribosomal RNA Intergenic Spacer Region of Several Seedborne Bacterial Pathogens of Rice", *Seed Science & Technology*, vol. 24, pp. 571–580, 1996.

Shakya, D.D., "Rapid Diagnosis of *Pseudomonas avenae* by Pathogenicity and Serology", *Korean J. Plant Pathology*-(Abstract), vol. 3, p. 300, 1987.

* cited by examiner

Forward Primers:
    5'-GTCGGTGCTAACGACATGG-3' (SEQ ID NO:1)

5'-GGAAGAATTCGGTGCTACCC-3' (SEQ ID NO:3)

5'-CCTCCACCAACCAATACGCT-3' (SEQ ID NO:5)

Reverse Primers:
    5'-AGACATCTCCGCTTTCTTTCAA-3' (SEQ ID NO:2)

5'-TCGTCATTACTGAATTTCAACA-3' (SEQ ID NO:4)

5'-CATGCTCTTAGTCACTTGACCCTA-3' (SEQ ID NO:6)

Probe:
    5'-CGGTAGGGCGAAGAAACCAACACC-3' (SEQ ID NO:7)

Fig. 1A

```
Aac  GGTGAAGTCG TAACAAGGTA GCCGTATCGG AAGGTGCGGC TGGATCACCT CCTTTCT--G   58
Aaa  GGTGAAGTCG TAACAAGGTA GCCGTATCGG AAGGTGCGGC TGGATCACCT CCTTTCTAAG   60
                                                    SEQ ID:3
Aac  GAAAACAGCA TTCATATTG AACGCCCACT CTTATCGGTT GTTGGAAGAA TTCGGTGCTA   118
Aaa  GAAAACAGCA TTCATATTG AACGCCCACA CTTATCGGTT GTTGGAAGAA GTCGGTGCTA   120
                                                              SEQ ID:1
Aac  CCCGACATGG GTCTGGTAGC TCAGCTGGTT AGAGCACCGT CTTGATAAGG CTGG--GGTC   176
Aaa  AC-GACATGG GTCT-GTAGC TCAGCTGGTT AGAGCACCGT CTAGATAAGG CGGGGAGTCG   178

Aac  GTTGGTTCGA GCCCAACTAG ACCCACCAAA TCTTCCGAAC ATAAGATGCG AGGA--TCAG   234
Aaa  TTGGGTTCGA GCCCAACTCG ACCCACCAAA TCTTCCGAAC ATAAGATGCG AGGAATCAAG   238
              tRNA^Ala
Aac  TGGGGGATTA GCTCAGCTGG GAGAGCACCT GCTTTGCAAG CAGGGGGTCG TCGGTTCGAT   294
Aaa  TGGGGGATTA GCTCAGCTGG GAGAGCACCT GCTTTGCAAG CAGGGGGTCG TCGGTTCGAT   298
              SEQ ID:5                       SEQ ID:7
Aac  CCCGTCATCC TCCA-CCAAC CAATACGCTC TGCGGTAGGG CGAAGAAACC AACACCAAAG   353
Aaa  CCCGTCATCC TCCACCCAAC CAATATGTCC TGCGGTAGGG CAAAGAAACT AACACCAAAG   358

Aac  CGGCTTCGCG -AGAGGCCTC TTTGTTGTTG GTCCGGTATA GACCGGATCA ATCGGCTGTT   412
Aaa  CGGCTTCGCG AAGAGGCCTC TTTGTTGTTG GTCCGGTATA GACCGGGTCA ATCGGCTGTT   418

Aac  CTTTAAAAAT TCATAGAGTC GAATCAGCGT TGCCGGCGGA AAGCAGGAAA CTGCA-CCGT   471
Aaa  CTTTAAAAAT TCATAGAGTC GAATCAGCGT TGCCGGCGGA AAGCAGGAAA CTGCATCCGT   478

Aac  GCCGCCGGTG ACAAAAATTT GATTGCGTCA AAACGAATAT TCAATT-GAG CGAAAGCTTG   530
Aaa  GCCGTCGGCA ACAAAAATTT GATTGCGTCC AAACGAATAT TCAATTGGAG CGAAAGCTGA   538
          "SEQ ID:4"
Aac  TTGAAATTCA GTAATGACGA ATTGTTCTC- TAGGTAGCAA TACCGCAAGA AGAATT-CAC   588
Aaa  TCGAAATTCA GTAATGACGA ATTGTTCTCT TAGGTAGCAA TACCCGAAGA AGAATTACAC   598

Aac  ATTACGGCA- TAACGCGCGA AGTGAAAGAC CTCGCAAGTC CTTGAAAGAA AGCGGAGATT   647
Aaa  ATTACGGCAT TAACGCGCGA TGTGAAAGAC CTCGCAAGTC CTTGAAAGAA AGCGGAGATG   658
                                                  "SEQ ID:6"   "SEQ ID:2"
Aac  TCTCGCTAGA GATTTCAAAG TTTTAGGGTC AAGTGACTAA GAGCATGTGG TGGATGCCTT   707
Aaa  TCTCGCAAGA GATGTCAA-- GTTATAGGTC AAGTGACTAA GAGCATGTGG TGGAT--CCT   714

Aac  GGCGATGATA GGCGACGAAA GACGTGATAG CCTGCGATAA   SEQ ID:8           747
Aaa  TGCGATGATA -GCGACGAAA GACGTGATAG CCTGCGATAA   SEQ ID:9           753
```

Fig. 1B

```
Rice          TCTGGAAAACAGCATTCAATATTGAACGCCCACACTTATCGGTTGTTGGA  50
Corn          ..................................................  50
Rescue grass  ..................................................  50
Wheat grass   ..................................................  50

Rice          AGAAGTCGGTGCTAACCGACATGGGTCTGTAGCTCAGCTGGTTAGAGCAC 100
Corn          .................................................. 100
Rescue grass  .................................................. 100
Wheat grass   .................................................. 100

Rice          CGTCTTGATAAGGCGGGGGTCGTTGGTTCGAGCCCAACTAGACCCACCAA 150
Corn          .................................................. 150
Rescue grass  .................................................. 150
Wheat grass   .................................................. 150

Rice          ATCTTCCGAACATAAGATGCGAGGATTAGT GGGGATTAGCTCAGCTGGG  200
Corn          .............................C.................... 200
Rescue grass  .............................C.................... 200
Wheat grass   .............................C.................... 200

Rice          AGAGCACCTGCTTTGCAAGCAGGGGGTCGTCGGTTCGATCCCGTCATCCT  250
Corn          .................................................. 250
Rescue grass  .................................................. 250
Wheat grass   .................................................. 250
              SEQ ID NO:10              SEQ ID NO:11
Rice          CCA CCAACCAAGATGCCCTGCGGTAGGGCGA-GAAACTAACACCAAAGCG 299
Corn          ...........T....T...............A.A............... 300
Rescue grass  ...........T....T.................................. 299
Wheat grass   ...........T....T.................................. 299

Rice          GCTTCGCAAGAGGCCTCTTTGTTGTTGGTCCGGTATAGACCGGGTCAATC 349
Corn          .................................................. 350
Rescue grass  ......G........................................... 349
Wheat grass   ......G........................................... 349

Rice          GGCTGTTCTTTAAAAATTCATAGAGTCGAATCAGCGTTGTCGGCGGAAAG 399
Corn          ...........................................C...... 400
Rescue grass  ...........................................C...... 399
Wheat grass   ...........................................C...... 399
                                          "SEQ ID NO:16"
Rice          CAGGAAACTGCACCGTGCCGTCGGCAACAAAAATTTGATTGCGTCAAAAC 449
Corn          .................................................. 450
Rescue grass  ............................TG.................... 449
Wheat grass   ............................TG.................... 449
                                                       "SEQ ID NO:12"
Rice          GAATATTCAATTGAGCGAAAGCTGATTGAAGTTCAGTAATGACGAATTGT 499
Corn          ................................A................. 500
Rescue grass  ....G.......-A..................A................. 498
Wheat grass   ....G.......-A..................A................. 498

Rice          TCTCTAGGTAGCAATACCGAAGAAAAATTCACATTACGGCATAACGCGCG 549
Corn          ..............................G................... 550
Rescue grass  ..............................G................... 548
Wheat grass   ..............................G................... 548

Rice          AGGTGAAAGACCTCGCAAGTCCTTGAAAGAAAGCGGAGATGTCTCGCAAG 599
Corn          .................................................. 600
Rescue grass  ...............................G.................. 598
Wheat grass   ...............................G.................. 598
                                                             619
Rice          AGATGTCAAAGTTATAGGGT  SEQ ID NO:13                   620
Corn          ....................  SEQ ID NO:14                   618
Rescue grass  ....................  SEQ ID NO:15                   618
Wheat grass   ....................  SEQ ID NO:15
```

FIG. 4

SEQUENCE LISTING

<160> NUMBER OF SEQ ID NOS: 16

<210> SEQ ID NO 1
<211> LENGTH: 19
<212> TYPE: DNA
<213> ORGANISM: Acidovorax avenae

<400> SEQUENCE: 1
gtcggtgcta acgacatgg                                          19

<210> SEQ ID NO 2
<211> LENGTH: 22
<212> TYPE: DNA
<213> ORGANISM: Acidovorax avenae

<400> SEQUENCE: 2
agacatctcc gctttctttc aa                                      22

<210> SEQ ID NO 3
<211> LENGTH: 20
<212> TYPE: DNA
<213> ORGANISM: Acidovorax avenae subsp. citrulli

<400> SEQUENCE: 3

-continued

<210> SEQ ID NO 4
<211> LENGTH: 22
<212> TYPE: DNA
<213> ORGANISM: Acidovorax avenae subsp. citrulli

<400> SEQUENCE: 4
tcgtcattac tgaatttcaa ca                                      22

<210> SEQ ID NO 5
<211> LENGTH: 20
<212> TYPE: DNA
<213> ORGANISM: Acidovorax avenae subsp. citrulli

<400> SEQUENCE: 5
cctccaccaa ccaatacgct                                         20

<210> SEQ ID NO 6
<211> LENGTH: 24
<212> TYPE: DNA
<213> ORGANISM: Acidovorax avenae subsp. citrulli

<400> SEQUENCE: 6
catgctctta gtcacttgac ccta                                    24

<210> SEQ ID NO 7
<211> LENGTH: 24
<212> TYPE: DNA
<213> ORGANISM: Acidovorax avenae subsp. citrulli

<400> SEQUENCE: 7
cggtagggcg aagaaaccaa cacc                                    24

<210> SEQ ID NO 8
<211> LENGTH: 747
<212> TYPE: DNA
<213> ORGANISM: Acidovorax avenae subsp. citrulli

<400> SEQUENCE: 8
ggtgaagtcg taacaaggta gccgtatcgg aagtgcggc tggatcacct cctttctgga       60
aaacagcatt caatattgaa cgcccactct tatcggttgt tggaagaatt cggtgctacc     120
cgacatgggt ctggtagctc agctggttag agcaccgtct tgataaggct ggggtcgttg     180
gttcgagccc aactagaccc accaaatctt ccgaacataa gatgcgagga tcagtggggg     240
attagctcag ctgggagagc acctgctttg caagcagggg gtcgtcggtt cgatcccgtc     300
atcctccacc aaccaatacg ctctgcggta gggcgaagaa accaacacca aagcggcttc     360
gcgagaggcc tctttgttgt tggtccggta tagaccggat caatcggctg ttctttaaaa     420
attcatagag tcgaatcagc gttgccggcg gaaagcagga aactgcaccg tgccgccggt     480
gacaaaaatt tgattgcgtc aaaacgaata ttcaattgag cgaaagcttg ttgaaattca     540
gtaatgacga attgttctct aggtagcaat accgcaagaa gaattcacat tacggcataa     600
cgcgcgaagt gaaagacctc gcaagtcctt gaaagaaagc ggagatttct cgctagagat     660
ttcaaagttt tagggtcaag tgactaagag catgtggtgg atgccttggc gatgataggc     720
gacgaaagac gtgatagcct gcgataa                                        747

<210> SEQ ID NO 9
<211> LENGTH: 753

```
<212> TYPE: DNA
<213> ORGANISM: Acidovorax avenae subsp. avenae

<400> SEQUENCE: 9
ggtgaagtcg taacaaggta gccgtatcgg aagtgcggc tggatcacct cctttctaag      60
gaaaacagca ttcaatattg aacgcccaca cttatcggtt gttggaagaa gtcggtgcta     120
acgacatggg tctgtagctc agctggttag agcaccgtct agataaggcg gggagtcgtt     180
gggttcgagc ccaactcgac ccaccaaatc ttccgaacat aagatgcgag gaatcaagtg     240
ggggattagc tcagctggga gagcacctgc tttgcaagca gggggtcgtc ggttcgatcc     300
cgtcatcctc cacccaacca atatgtcctg cggtagggca agaaactaa caccaaagcg      360 gcttcgcgaa gaggcctctt tgttgttggt ccggtataga ccgggtcaat cggctgttct     420
ttaaaaattc atagagtcga atcagcgttg ccggcggaaa gcaggaaact gcatccgtgc     480
cgtcggcaac aaaaatttga ttgcgtccaa acgaatattc aattggagcg aaagctgatc     540
gaaattcagt aatgacgaat tgttctctta ggtagcaata cccgaagaag aattacacat     600
tacggcatta acgcgcgatg tgaaagacct cgcaagtcct tgaaagaaag cggagatgtc     660
tcgcaagaga tgtcaagtta taggtcaagt gactaagagc atgtggtgga tccttgcgat     720
gatagcgacg aaagacgtga tagcctgcga taa                                  753

<210> SEQ ID NO 10
<211> LENGTH: 20
<212> TYPE: DNA
<213> ORGANISM: Acidovorax avenae subsp. avenae

<400> SEQUENCE: 10
gtcatcctcc accaaccaag                                                  20

<210> SEQ ID NO 11
<211> LENGTH: 20
<212> TYPE: DNA
<213> ORGANISM: Acidovorax avenae subsp. avenae

<400> SEQUENCE: 11
agatgccctg cggtagggcg                                                  20

<210> SEQ ID NO 12
<211> LENGTH: 23
<212> TYPE: DNA
<213> ORGANISM: Acidovorax avenae subsp. avenae

<400> SEQUENCE: 12
agaacaattc gtcattactg aac                                              23

<210> SEQ ID NO 13
<211> LENGTH: 619
<212> TYPE: DNA
<213> ORGANISM: Acidovorax avenae subsp. avenae

<400> SEQUENCE: 13
tctggaaaac agcattcaat attgaacgcc cacacttatc ggttgttgga agaagtcggt      60
gctaaccgac atgggtctgt agctcagctg gttagagcac cgtcttgata aggcgggggt    120
cgttggttcg agcccaacta gacccaccaa atcttccgaa cataagatgc gaggattagt    180
gggggattag ctcagctggg agagcacctg ctttgcaagc agggggtcgt cggttcgatc    240
ccgtcatcct ccaccaacca agatgccctg cggtagggcg agaaactaac accaaagcgg    300
```

-continued

```
cttcgcaaga ggcctctttg ttgttggtcc ggtatagacc gggtcaatcg gctgttcttt      360
aaaaattcat agagtcgaat cagcgttgtc ggcggaaagc aggaaactgc accgtgccgt      420
cggcaacaaa atttgattg cgtcaaaacg aatattcaat tgagcgaaag ctgattgaag       480
ttcagtaatg acgaattgtt ctctaggtag caataccgaa gaaaaattca cattacggca     540
taacgcgcga ggtgaaagac ctcgcaagtc cttgaaagaa agcggagatg tctcccaaga    600
gatgtcaaag ttatagggt                                                  619
```

<210> SEQ ID NO 14
<211> LENGTH: 620
<212> TYPE: DNA
<213> ORGANISM: Acidovorax avenae subsp. avenae

<400> SEQUENCE: 14

```
tctggaaaac agcattcaat attgaacgcc cacacttatc ggttgttgga agaagtcggt      60
gctaaccgac atgggtctgt agctcagctg gttagagcac cgtcttgata aggcggggt      120 cgttggttcg agcccaacta gacccaccaa atcttccgaa cataagatgc gaggatcagt     180
gggggattag ctcagctggg agagcacctg ctttgcaagc aggggtcgt cggttcgatc      240 ccgtcatcct ccaccaacca atatgtcctg cggtagggca agaaactaa caccaaagcg      300 gcttcgcaag aggcctcttt gttgttggtc cggtatagac cgggtcaatc ggctgttctt     360
taaaaattca tagagtcgaa tcagcgttgc cggcggaaag caggaaactg caccgtgccg    420
tcggcaacaa aatttgattt gcgtcaaaac gaatattcaa ttgagcgaaa ctgattgaa      480 attcagtaat gacgaattgt tctctaggta gcaataccga agaagaattc acattacggc    540
ataacgcgcg aggtgaaaga cctcgcaagt ccttgaaaga aagcggagat gtctcccaag    600
agatgtcaaa gttatagggt                                                  620
```

<210> SEQ ID NO 15
<211> LENGTH: 618
<212> TYPE: DNA
<213> ORGANISM: Acidovorax avenae subsp. avenae

<400> SEQUENCE: 15

```
tctggaaaac agcattcaat attgaacgcc cacacttatc ggttgttgga agaagtcggt      60
gctaaccgac atgggtctgt agctcagctg gttagagcac cgtcttgata aggcggggt      120 cgttggttcg agcccaacta gacccaccaa atcttccgaa cataagatgc gaggatcagt     180
gggggattag ctcagctggg agagcacctg ctttgcaagc aggggtcgt cggttcgatc      240 ccgtcatcct ccaccaacca atatgctctg cggtagggcg agaaactaac accaaagcgg    300
cttcgcgaga ggcctctttg ttgttggtcc ggtatagacc gggtcaatcg gctgttcttt    360
aaaaattcat agagtcgaat cagcgttgcc ggcggaaagc aggaaactgc accgtgccgt    420
cggtgacaaa atttgattg cgtcaaaacg aatgttcaat aagcgaaagc tgattgaaat     480
tcagtaatga cgaattgttc tctaggtagc aataccgaag aagaattcac attacggcat    540
aacgcgcgag gtgaaagacc tcgcaagtcc ttgaaagaag gcggagatgt ctcccaagag    600
atgtcaaagt tatagggt                                                   618
```

<210> SEQ ID NO 16
<211> LENGTH: 22

-continued

```
<212> TYPE: DNA
<213> ORGANISM: Acidovorax avenae subsp. avenae

<400> SEQUENCE: 16
aatttttgtt gccgacggca cg                                              22
```

PCR PRIMERS FOR DETECTION AND IDENTIFICATION OF PLANT PATHOGENIC SPECIES, SUBSPECIES, AND STRAINS OF ACIDOVORAX

The present application is a continuation-in-part of application Ser. No. 09/393,877, filed Sep. 10, 1999 now U.S. Pat. No. 6,146,834, which is hereby incorporated by reference in its entirety.

BACKGROUND OF THE INVENTION

1. Field of the Invention

The species *Acidovorax avenae*, formerly classified as *Pseudomonas avenae*, contains different subspecies pathogenic to several hosts including oat, corn, millet, wheat, sugarcane, rice, orchid, konjaci, and Cucurbitaceae plants including melon, watermelon, and squash. This invention relates to novel PCR primers which can be used to detect plant pathogenic *Acidovorax avenae* species and to distinguish among the pathogenic subspecies and strains, particularly to distinguish (1) *A. avenae* from other bacteria, (2) *A. avenae* subsp. *citrulli* (infects only Cucurbitaceae) from other subspecies and (3) rice strains of *A. avenae* subsp. *avenae* from other strains originating from other plants as well as from other subspecies of *A. avenae.*

2. Description of the Relevant Art

The bacterium *A. avenae* subsp. avenaecauses bacterial stripe of rice, leaf blight of oats, red stripe disease of sugarcane and millet, and brown stripe of *Setaria italica*. The organism was originally described as *Pseudomonas avenae* by Manns in 1909 (*Ohio Agric. Exp. Stn. Res. Bull.* 210: 91–167) as the causal agent of leaf blight on oats in Ohio. Another organism, *P. alboprecipitans*, described by Rosen in 1922 on foxtail (*Ann. Mo. Bot. Gard.* 9:333–402) and on corn in 1926 (*Phytopathology* 16:241–267) was later shown to be synonymous with *P. avenae* (Schaad et al. 1975. *Int J. Syst Bacteriol.* 25:133–137). On rice, the organism has been previously referred to as *P. setariae* or *P. panici* (Goto. 1964. *Bull. of Faculty of Agriculture*, Shizuoka University 14: 3–10) and on sugarcane as *P. rubrilineans* (Martin et al. 1989.), the causal agent of red stripe diseases of sugarcane (C. Ricaud et al. (Eds), Elsevier, The Netherlands, pp. 80–95). *Acidovorax avenae* subsp. *citrulli* causes bacterial blight and fruit blotch of watermelon and melon. The organism was originally described by Schaad et al. (1978. *Int. J. Syst. Bacteriol.* 28:117–125) in plant introduction breeding lines of watermelon in Georgia as *P. pseudoalcaligenes* subsp. *citrulli*. A closely related organism, *A. avenae* subsp. *cattleyae* occurs on orchids (Ark and Thomas. 1946. *Phytopathology* 36:695–698) and *A. konjaci* (Goto, M. 1983. *Int J. Syst. Bacteriol.* 33:539–545) occurs on konjac (*Amorphophalus konjaci* Koch).

As the host range of *A. avenae* subsp. *avenae* is wide to monocotyledonous and dicotyledonous plants, it has been thought to be polyxenic. However, individual strains of the pathogen infect only one or a few host species (Kadota, I. 1996. *Bulletin of the Hokuriku National Agricultural Experiment Station* 38:113–171; Nishiyama et al. 1979. *Ann. Phytopathol. Soc. Jpn.* 45:25–31). For example, rice strains can infect rice but not other monocotyledonous plants including finger millet, whereas finger millet strain cannot infect rice plants. Furthermore, the heterogeneity of rice strains and other plant strains of the bacterium has been suggested based on the biochemical characteristics and the protein profiles of the cells. Even though the reclassification of previous *P. avenae* strains to *A. avenae* subsp. *avenae* has been widely accepted, a certain degree of pathogenic, serological, and genomic, as well as phenotypic, heterogeneity still exists among reported strains of *A. avenae* subsp. *avenae* subspecies. Pathogenicity of *A. avenae* subsp. *avenae* strains specific for rice particularly differs from non-rice strains of *A. avenae* subsp. *avenae*. It has been thought, therefore, that rice strains of *A. avenae* subsp. *avenae* are different from other plant strains. However, hitherto there is no sensitive and specific means which can detect all the strains of *A. avenae* subsp. *avenae* which have originated from different hosts and thus satisfy the current taxonomic situation at the subspecies level.

Phylogenetically, *A. avenae* is included in the new "acidovorans" DNA-rRNA homology group (Willems et al. 1992. *Int J. Syst Bacteriol.* 42:107–119). This group contains many pathogens previously classified in the non-fluorescent pseudomonad group, including *P. avenae* Manns 1909 (*Ohio Agric. Exp. Stn. Res. Bull.* 210:91–167), *P. cattleyae* Savulescu 1947 (Pavarino. 1911. *Atti Accad. Lincei* 20:233–237), *P. pseudoalcaligenes* subsp. *citrulli* (Schaad et al. 1978, supra), *P. pseudoalcaligenes* subsp. *konjaci* (Goto, 1983, supra) and *P. rubrilineans* (Lee et al. 1925. Red Stripe Disease. Pamphlet of Hawaiian Sugar Planters Association). Recently, all of these bacteria have been reclassified as subspecies of *A. avenae*, i.e., *A. avenae* subsp. *avenae, A. avenae* subsp. *cattleyae*, and *A. avenae* subsp. *citrulli*, on the basis of the results of DNA-DNA hybridization, DNA-rRNA hybridizations, polyacrylamide gel electrophoresis of whole-cell proteins, and a numerical analysis of carbon assimilation tests (Willems et al., supra).

*A. avenae* subsp. *avenae* is one of the major seedborne bacterial pathogens of rice. Seeds infested with the pathogen are important sources of primary inoculum and a means of dissemination to new areas. Therefore, sensitive and simple detection methods are needed to screen seed lots. Presently, the only reliable method to identify the *A. avenae* pathogens is to isolate them on agar media and confirm their presumptive identification by time consuming and expensive pathogenicity tests. Although a few methods have been used for the detection of *A. avenae* subsp. *avenae*, none has been optimized for selectively detecting the bacterium from rice seeds. Serological methods and a rapid pathogenicity test have been used for routine detection of this pathogen in rice seeds (Kadota et al., supra; Shakya. 1987. *Korean J. Plant Path.* 3:300; Zeigler et al. 1989. *Intl. Rice Res. Newsletter* 14:27–28). However, in addition to the issues of specificity and sensitivity, serological techniques have the distinct disadvantage of not being able to provide information on viability and pathogenicity of the seedborne inoculum. In rice, *A. avenae* subsp. *avenae* can be recovered from both diseased, or asymptomatic, apparently healthy seeds. However, identification is difficult, because the organism is frequently overgrown by other bacterial pathogens of rice, such as Pantoea (Erwinia) herbicola, Burkholdera (Pseudomonas) glumae, *B. fuscovaginae*, or *P. syringae* pv. *syringae*. These pathogens are recognized as producing distinct disease symptoms, but field diagnosis is very difficult. In such cases, detection and identification is based on pathogen isolation, through the use of semiselective media, and on pathogenicity tests which discriminate between the various pathogens. However, the presence of coexisting epiphytes such as *P. fulva, P. corrugata, P. putida*, and *P. fluorescens* in/on rice seed makes isolation difficult. Furthermore, rice seedlings are difficult to grow and symptoms on seedlings are often non-discriminating. Several methods of identification of *A. avenae* subsp. *avenae* have been proposed including growth and isolation on semiselective agar media and serology (Shakya, supra). None have achieved much success. The disease cycle, therefore, has not been clarified, because the symptoms are masked after the four or five leaf stage and no adequate techniques are available for monitoring the pathogen in rice plants. Further, there is currently no reliable, routine method available for detecting A. avenae in rice seeds. More sensitive and specific methods are needed to confirm the identification, especially in seed health evaluations.

Similar problems exist for watermelon and melons. Although originally described as a seedling disease, watermelon fruit blotch has emerged as a serious disease of mature fruit. Complete losses of production fields often occur due to fruit rot. Like most seedborne bacteria, control is based primarily on seed health testing. Because of the seriousness of watermelon fruit blotch, nearly all watermelon seed lots must be assayed for A. avenae subspec. citrulli. This involves soaking 30,000 seeds and attempting to isolate the organism on agar media or inoculating plants with the seed soakate. Neither method is very efficient and both are relatively expensive. Little or no resistance to the pathogen exists.

Bacterial stripe causes great losses in rice seedling beds throughout Asia. Thus far, the disease has not been observed in the U.S. However, the potential risk of the dissemination of the bacterial stripe pathogen in international exchange of germplasm of rice and corn is a serious concern. There is presently no way to separate infected seeds and contaminated seeds. Therefore, there is a need to develop reagents and methods for detecting A. avenae subspecies specifically, rapidly, and directly from biological samples. Such methods and reagents are valuable tools for monitoring natural disease spread, tracking the seedborne bacteria in field studies, and detecting the presence of the bacterium in seed lots entering A. avenae-free areas.

Polymerase chain reaction (PCR) has been shown to be highly sensitive and the method is commonly used to detect and identify bacteria. A PCR method has been described for detecting the pathogen A. avenae subsp. citrulli, in seeds; however, the primers are not unique and the method has not gained industry acceptance (Minsavage et al. 1995. Ann. Mtg. Amer. Phytopath. Abstract 379). Thus, there exists a need for specific primers and methods capable of specifically identifying and differentiating pathogenic A. avenae subspecies and strains.

SUMMARY OF THE INVENTION

We have discovered oligonucleotide sequences which are capable of amplifying DNA fragments specific for identifying the two closely related pathogens when used in a simple and rapid PCR assay. One set of oligonucleotide sequences are specific for identifying all but one subspecies of A. avenae; other sets are useful for selectively and specifically identifying either the highly destructive watermelon fruit blotch pathogen, A. avenae subsp. citrulli or the strains of A. avenae subsp. avenaepathogenic for rice. These two subspecies avenaeand citrulli are phenotypically very similar and are very difficult to differentiate. In addition, two other sets of primers and probes specific for identifying A. avenae subsp. citrulli have been designed for the TaqMan (Perkin Elmer) 7700 detection system. One of these primers is the same as described for detecting A. avenae subsp. citrulli by classical PCR, whereas the other primers and probe are different.

In accordance with this discovery, it is an object of the invention to provide the novel oligonucleotides for use as primers for PCR assays for the specific detection and identification of plant pathogenic subspecies of A. avenae.

It is also an object of the invention to provide primers for the specific detection and identification of the watermelon fruit blotch pathogen, A. avenae subsp. citrulli, thereby differentiating A. avenae subsp. citrulli from other A. avenae subspecies.

It is an additional object of the invention to provide primers for the specific detection and identification of the strains of A. avenae subsp. avenaepathogenic for rice, thereby differentiating the rice strains of A. avenae subsp. avenaefrom A. avenae subsp. avenaeoriginating from other plants and from other subspecies of A. avenae.

It is another object of the invention to provide PCR assay methods utilizing the novel primers.

It is a further object of the invention to provide a screening method for distinguishing subspecies of A. avenae by utilizing two sets of primers.

It is yet an additional object of the invention to provide a method for assaying seeds for presence of A. avenae subsp. citrulli and for monitoring seed treatment protocols utilizing the novel primers.

It is still another object of the invention to provide a method for assaying seeds for presence of strains of A. avenae subsp. avenaethat are pathogenic for rice and for monitoring seed treatment protocols utilizing the novel primers.

It is an added object of the invention to provide a kit for use in the detection of A. avenae subspec. citrulli.

It is another added object of the invention to provide a kit for use in the detection of the rice strains of A. avenae subspec. avenae.

Other objects and advantages of the invention will become readily apparent from the following description.

BRIEF DESCRIPTION OF THE DRAWINGS

FIG. 1A shows the nucleotide sequence of the selected primers SEQ ID NO:1 and SEQ ID NO:2 of *Acidovorax avenae* subsp. avenaeCOA1 and the selected primers SEQ ID NO:3, SEQ ID NO:4, SEQ ID NO:5, SEQ ID NO:6 and the probe (SEQ ID NO:7) of *A. avenae* subsp. *citrulli* ATCC 29625.

FIG. 1B shows the nucleotide sequence of the intergenic spacer region (ISR); the shaded area represents the ISR sequence of *Acidovorax avenae* subsp. *citrulli* (SEQ ID NO:8; Aac, upper) and *Acidovorax avenae* subsp. *avenae* (SEQ ID NO:9; Aaa, lower). The unshaded area represents tRNA$^{Ala}$ gene sequences. Sequences that are disclosed in the Sequence Listing as having SEQ ID NOs: 2, 4, and 6 are complementary to the reverse orientation of the sequences which are underlined and identified as "SEQ ID NO:2", "SEQ ID NO:4", and "SEQ ID NO:6" in FIG. 1B. SEQ ID NOs: 1, 3, 5, and 7 are also underlined and appear in FIG. 1B as they are disclosed in the Sequence Listing.

FIG. 2A: Lane 1, 100 bp ladder; Lane 2, A. avenae subsp. avenae (Aaa) ATCC 19822; Lane 3, Aaa 39463d; Lane 4, Aaa Nepal; Lane 5, Aaa 39462c; Lane 6, Aaa 39461 g; Lane 7, A. avenae subsp. citrulli, (Aac) 40584 isolate B3; Lane 8, Aac 40565 A; Lane 9, Aac 40560 isolate 8; Lane 10, Aac 40565 b; Lane 11, Aac 40556 isolate 2; Lane 12, Aac 40582 isolate A1; Lane 13, Aac 40560 isolate 6; Lane 14, Aaa 39459 b; Lane 15, Aaa 39128 c; Lane 16, Aac 40582 isolate e/2; Lane 17, Aac 40582 isolate al; Lane 18, Aac 40581 isolate B; Lane 19, Aac 40580 isolate A; Lanes 20 and 21, 100 bp ladder; Lane 22, Aaa ATCC 19822; Lane 23, Aac 40580 isolate A#2; Lane 24, Aaa 391230; Lane 25, Acc 40560 isolate 4; Lane 26, Acc 40580 isolate B; Lane 27, Acc 40584 isolate A2; Lane 28, Aac 40581 isolate A; Lane 29, Aac 40587; Lane 30, Aac, 405708 isolate A; Lane 31, Kihupi 40565; Lane 32, Aaa 39122 C; Lane 33, Aaa 39460 1; Lane 34, Pca 1; Lane 35, Pca 2; Lane 36, Pca 3; Lane 37, Pca 4; Land 38, Pca 5; Lane 39, Pca 6; Lane 40, 100 bp ladder. FIG. 2B: Lanes 1 and 18,100 bp ladder; Lanes 2 and 3, *A. avenae* subsp. *citrulli*, Aac 01; Lanes 4 and 5, *A. avenae* subsp. *cattleyae*; Lanes 6 and 7, *Burkholderia glumae*; Lanes 8 and 9, *A. avenae* subsp. *avenae* COA-1; Lanes 10 and 11, *A. avenae* subsp. *citrulli*, Aac 130; Lanes 12 and 13, *A. avenae* subsp. *cattleyae* PC-21; Lanes 14 and 15, *B. glumae* COG-2; and Lanes 16 and 17, *A. avenae* subsp. avenaeCOA-4.

FIG. 4 shows the alignment of the 16S–23S rDNA spacer sequences of *Acidovorax avenae* subsp. *avenae* Caa4 from rice (SEQ ID NO: 13), ATCC19860 from corn (SEQ ID NO:14), MAFF301031 from rescuegrass (SEQ ID NO:15), and MAFF301027 from wheatgrass (SEQ ID NO:15) and the location of each primer. The boxed sequence represents the tRNA Ala-coding gene. The sequences disclosed in the Sequence Listing as having SEQ ID NO:12 and SEQ ID NO:16 are complementary to the reverse orientation of the sequences which are identified as "SEQ ID NO:12" and "SEQ ID NO:16". SEQ ID NOs:10 and 11 appear in FIG. 4 as they are disclosed in the Sequence Listing.

DETAILED DESCRIPTION OF THE INVENTION

Figure 2A:
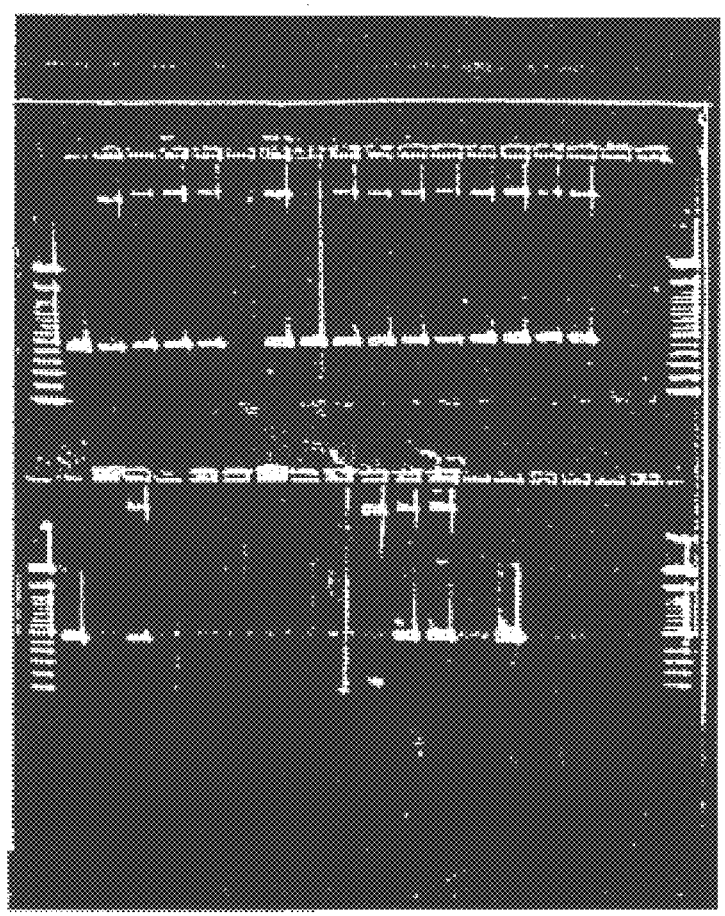
FIGS. 2A–2B are images of ethidium bromide stained gels showing a 550 bp PCR product formed by primers SEQ ID NO:1 and SEQ ID NO:2 (FIG. 2A) and a 450 bp PCR product formed by primers SEQ ID NO:3 and SEQ ID NO:4 (FIG. 2B.

Polymerase chain reaction (PCR) has been shown to be a highly sensitive and rapid method for detecting and identifying bacteria. The invention provides for PCR primers, methods, and kits useful for detecting subspecies and strains of the pathogen *Acidovorax avenae* in or on seeds. It further provides for differentiating *A. avenae* subsp. *citrulli* from other *A. avenae* subspecies and for differentiating the rice strains of *A. avenae* subsp. *avenae* from *A. avenae* subsp. *avenae* strains originating from plants other than rice and as well as from other subspecies of *A. avenae*.

Strategy for Obtaining Specific Primers for *A. avenae* Subspecies

Several primers and primer sets have been identified as effective for amplifying particular *A. avenae* subspecies and differentiating between subspecies, when used in the standard PCR method (Mullis. 1987. U.S. Pat. No. 4,683,202) or the BIO-PCR method (U.S. patent application Ser. No. 08/344,085, herein incorporated by reference; Schaad et al. 1995. *Pytopath*. 85:243–248). Variations in length and sequences of the 16S–23S rDNA intergenic spacer region (ISR) of several bacteria have recently been targeted for use in discriminating among strains at the species and subspecies levels. These spacers are short stretches of DNA located between the 16S and 23S genes in prokaryotic rRNA loci and usually contain one or more tRNA genes. Elements important to transcription and noncoding of DNA that apparently are not functional should exhibit a considerable degree of sequence variation. Thus, such variable regions make sequences of ISRs good markers to measure short-term phylogeny, i.e., a fast molecular clock. The characterization of the ISR of *A. avenae* and other bacterial pathogens of rice suggested that the ISR contained sequences unique to *A. avenae* (Kim et al. 1996. *Seed Sci. & Technol.* 24:571–580). Therefore, the ISR of *A. avenae* was targeted as a possible source of DNA which would be specific for the different species and subspecies. The ISR sequences of *Acidovorax avenae* subsp. *citrulli* (SEQ ID NO:8) and *A. avenae* subsp. *avenae* (SEQ ID NO:9) are shown aligned in FIG. 1A; FIG. 4 shows the alignment of the ISR sequences of *Acidovorax avenae* subsp. *avenae* Caa4 from rice (SEQ ID NO: 13), ATCC19860 from corn (SEQ ID NO:14), MAFF301031 from rescuegrass (SEQ ID NO:15), and MAFF301027 from wheatgrass (SEQ ID NO:15). In particular, unique PCR primers were derived from sequences of a fragment of the ISR of the 16S–23S rDNA for rapid identification of all those subspecies of *A. avenae* from oats, rice, corn, millet, wheat, sugarcane, orchid, and watermelon, for the specific detection of the subspecies *citrulli* from watermelon, and for the specific detection of the rice strains of *A. avenae* subsp. *avenae*. These primers, when combined with BIO-PCR, should prove useful for sensitive detection of the pathogen in a seed health testing program for several diseases, including bacterial brown stripe of rice, leaf blight of oats, red stripe of sugar cane, bacterial leaf blight of corn and watermelon fruit blotch. Furthermore, rapid, conclusive, cost- and labor-efficient analysis can be performed when these unique primers and probes are combined with a BIO-PCR method employing the high throughput, real time TaqMan detection system.

A primer is preferably about eighteen to twenty-four nucleotides long. Primers can hybridize to a DNA strand with the coding sequence of a target sequence and are designated sense primers. Primers can also hybridize to a DNA strand that is the complement of the coding sequence of a target sequence; such primers are designated anti-sense primers. Primers that hybridize to each strand of DNA in the same location or to one another are known as complements of one another. Primers can also be designed to hybridize to a mRNA sequence complementary to a target DNA sequence and are useful in reverse transcriptase PCR.

Figure 2B:
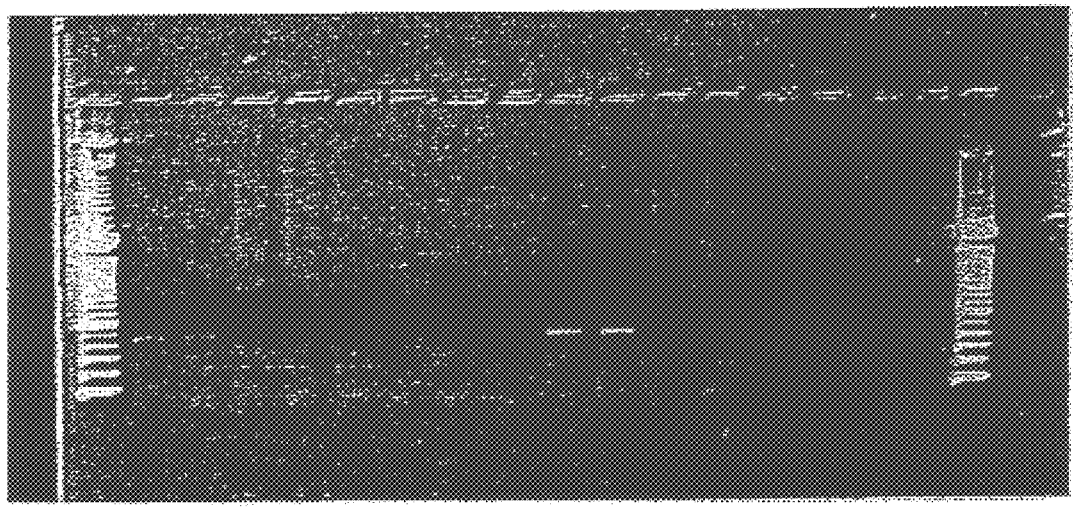

The novel primers of the invention hybridize to a target DNA sequence of *A. avenae* subspecies located in the 16S–23S rDNA ISR of 950-bp. The primers are specific for *A. avenae* subspecies and do not hybridize to other closely related microorganisms. The primers can therefore be used in methods and kits for detecting subspecies and strains of *A. avenae* in biological samples. The primers identified as SEQ ID NO:1 and SEQ ID NO:2 and the primer set comprising these primers are useful in an assay to detect the presence of *A. avenae* in a sample; specifically, any one or all of the subspecies, *A. avenae* subsp. *avenae, A. avenae* subsp. *cattleyae*, or *A. avenae* subsp. *citrulli*. The primers identified as SEQ ID NO:3 and SEQ ID NO:4 and the primer set comprising these primers distinguish *A. avenae* subsp. *citrulli* from *A. avenae* subsp. *avenae* and *cattleyae*. The primers identified as SEQ ID NO:10, SEQ ID NO:11, and SEQ ID NO:12 and the primer sets comprising these primers distinguish the rice strains of *A. avenae* subsp. *avenae* from *A. avenae* subsp. *avenae* strains originating from plants other than rice as well as from other subspecies of *A. avenae*. Thus, as shown in these examples, primers consisting of nucleotide sequences from the ISR of *Acidovorax avenae* species and strains can be used to identify and distinguish subspecies and strains of Acidovorax. Particular nucleotide sequences from the ISR of rice (SEQ ID NO: 13) which contain one or several nucleotide residues "unique" to the ISR of rice can be used as primers to identify the rice strains of *A. avenae* subsp. *avenae*, as for example, SEQ ID NOs: 10, 11, and 12. "Unique" nucleotide residue refers to a nucleotide residue which is different from that residue which occupies the same or corresponding position in any one of the closely related sequences identified by SEQ ID NO:8, 9, 14, 15, or 16, as aligned in FIG. 1B and FIG. 4. A primer useful for identifying subspecies or strains has one or more unique nucleotides that are easily identifiable. For example, when the ISRs as represented by SEQ ID NOs: 13, 14, 15, and 16 are aligned as in FIG. 4, "G" at position 162 in the rice ISR is observed to differ from "T" in the corresponding position in the ISRs of corn, resuegrass, and wheatgrass. The primer SEQ ID NO:10 ends in this unique "G" nucleotide and distinguishes the rice strains of *A. avenae* subsp. *avenae* from *A. avenae* subsp. *avenae* strains originating from plants other than rice. Another example, wherein the primer has unique internal residues, is SEQ ID NO:16 (5'-AATTTTTGTTGCCGACGGCACG-3') shown in FIG. 4. The unique internal nucleotides "C" and "A" in positions 424 and 425, respectively, distinguish the rice strains of *A. avenae* subsp. *avenae* from *A. avenae* subsp. *avenae* strains originating from rescuegrass and wheatgrass. Primers can comprise nucleotide sequences having other "unique" residues found in the ISRs identified by SEQ ID NOs: 8, 9, 13, 14, 15, and 16.

In addition, the primers of the invention are useful for employing BIO-PCR techniques for evaluating and monitoring the efficacy of treatments for eliminating the pathogenic *A. avenae* subspecies from seeds. Since BIO-PCR is based on detection of DNA from live cells obtained from agar in liquid media, neither contaminating DNA from dead cells or PCR inhibitors from plant materials pose a problem. Detection of *A. avenae* subsp. *citrulli* can be further optimized by utilizing the primers identified as SEQ ID NO:4, SEQ ID NO:5, and SEQ ID NO:6 and the primer sets comprising these primers, namely, primer set SEQ ID NOs:5 and 4 or primer set SEQ ID NOs:5 and 6 in the BIO-PCR method, combining BIO-PCR with the TaqMan detection system and employing the probe identified as SEQ ID NO:7. TaqMan is a PCR-based assay that utilizes an oligonucleotide probe containing a "fluorescent reporter"—"fluorescence quencher" pair, wherein the quencher molecule of the probe is designed to be located close enough to the reporter molecule to ensure that the fluorescence of the reporter molecule is quenched. The binding site of the probe is located between the PCR primers used to amplify the target polynucleotide. Preferably, PCR is carried out using Taq DNA polymerase, AMPLITAQ (Perkin-Elmer, Norwalk, Conn.). During strand extension by Taq DNA polymerase, the annealed probe containing the reporter/quencher pair is digested by the 5'→3' exonuclease activity of taq polymerase. Digestion of the probe results in the reporter molecule becoming separated from the quencher molecule; thus, the quencher molecule is no longer close enough to the reporter molecule to quench the reporter molecule's fluorescence. Therefore, as more and more annealed probes are digested during amplification, the number of unquenched reporter molecules in solution increases, resulting in a stronger and stronger fluorescent signal being produced during consecutive cycles. This use of BIO-PCR together with the TaqMan automated real-time fluorescence detection system results in the detection of as few as 2 cfu/ml. The primers of the invention may also be useful as hybridization probes.

Preparation of Primers

Genomic DNA was extracted from cultures of *A. avenae* subsp. avenaestrain COA1 and *A. avenae* subsp. *citrulli* strain 29625 in late logarithmic phase, as described by Prosen et al. (1993. *Pytopath*. 83:965–970). The amplification of the ISR was performed using the known primers R16-1 and R23-2R and the method described by Kim et al., supra. For *A. avenae* subsp. *avenae*, the amplified full length 950-bp ISR product was cloned into pGEM7f (GIBCO BRL). The resulting clone, pOA3, containing the 950-bp full length ISR insert was then sequenced. For *A. avenae* subsp. *citrulli*, the amplified full length 950-bp ISR product was cloned into pCR2.1 with TA cloning kit (INVITROGEN). The resulting clone, pCIT7, containing a 950-bp insert of full length ISR, was then sequenced.

The sequencing of the cloned 16S–23S ISR fragment was performed by the dideoxy-chain termination method using ABI PRISM 310 Genetic Analyzer and Dye Terminator Cycle Sequencing Core Kit (Perkin Elmer, Foster City, Calif.) following the manufacturer's protocol (Sanger et al. 1977. *Proc. Natl. Acad. Sci. USA* 74:5463–5467). From the ISR sequences, candidate primers were selected using the program OLIGO (National Biosciences, Hamel, Minn.) and synthesized commercially by GIBCO BRL (Frederick, Md.). The primers 5'-GTCGGTGCTAACGACATGG-3' (SEQ ID NO:1) and 5'-AGACATCTCCGCTTTCTTTCAA-3' (SEQ ID NO:2) of *A. avenae* subsp. *avenae* (FIG. 1A) and the primers 5'-GGAAGAATTCGGTGCTACCC-3' (SEQ ID NO:3) and 5'-TCGTCATTACTGAATTTCAACA-3' (SEQ ID NO: 4) of *A. avenae* subsp. *citrulli* (FIG. 1B) were used to amplify the ISR of 43 strains of *A. avenae*, 11 strains of *A. avenae* subsp. *citrulli*, four of *A. avenae* subsp. *cattleyae*, single strains of *A. konjaci* and *A. facilis*, 26 other known bacteria, and 27 unknown bacteria isolated from seeds. The specificity of each set of primers is illustrated in Table 1, below, and in FIGS. 2A and 2B. As shown in Table 1, for primers SEQ ID NO:1 and SEQ ID NO:2, a PCR product of approximately 550 bp was obtained for all strains of *A. avenae* subsp. *avenae* and *A. avenae* subsp. *citrulli* and the ATCC strain of *A. avenae* subsp. *cattleyae*. Three strains of *A. avenae* subsp. *cattleyae* and the single strain of *A. konjaci* were negative. All other bacteria, including 1–6 strains each of five other species of non-fluorescent pseudomonads (including 12 strains of Burkholderia), four fluorescent pseudomonads, two xanthomonads, two erwinea, and six strains of unknown bacteria from rice seed were negative. FIG. 2A also shows a 550 bp product obtained from strains of *A. avenae* subsp. avenaeand *A. avenae* subsp. *citrulli*. Primers SEQ ID NO:3 and SEQ ID NO:4 produced a 450-bp product with all strains of *A. avenae* subsp. *citrulli* specifically (FIG. 2B); all other bacteria were negative.

The combination of BIO-PCR with TaqMan assay methodology is a more rapid and labor- and cost-effective assay than standard PCR or BIO-PCR where the additional identification step of Southern analysis is required. The BIO-PCR/TaqMan combination assay utilizing the primer set comprising primer 5'-CCTCCACCAACCAATACGCT-3' (SEQ ID NO:5) together with either primer 5'-TCGTCATTACTGAATTTCAACA-3' (SEQ ID NO:4) or primer 5'-CATGCTCTTAGTCACTTGACCCTA-3' (SEQ ID NO:6) as detected with the probe: 5'-CGGTAGGGCGAAGAMCCAACACC-3' (SEQ ID NO:7) results in the specific identification of *A. avenae* subsp. *citrulli*.

TABLE 1

Species and strains and results of PCR with primers SEQ ID NOS: 1 & 2 of *Acidovorax avenae* subsp. *avenae* and with the primers SEQ ID NOS: 3 & 4 of *A. avenae* subsp. *citrulli*

| Bacterial strains | No. | Host | Source[a] | PCR-Amplification SEQ ID NOS: 1 and 2[b] | PCR-Amplification SEQ ID NOS: 3 and 4[c] |
|---|---|---|---|---|---|
| *A. avenae* subsp. *avenae* (*Pseudomonas avenae*) | | | | | |
| COA1–3 | 3 | rice | 1 | + | − |
| ATCC 19860 | 1 | corn | 2 | + | − |
| PA135–138 | 4 | corn | 3 | + | − |
| 3307–8Pav | 2 | corn | 3 | + | − |
| 3403Pav | 1 | vaseygrass | 3 | + | − |
| 3406Pav | 1 | corn | 3 | + | − |
| 3431Pav | 1 | millet | 3 | + | − |
| Nepal | 1 | rice | 4 | + | − |
| 39123a | 1 | rice | 4 | + | − |
| 39459–39463 | 5 | rice | 4 | + | − |
| 30150–11 | 10 | rice | 5 | + | − |
| 311056–58 | 3 | rice | 5 | + | − |
| (*P. rubrilineans*) | | | | | |
| ATCC 19307 | 1 | sugarcane | 2 | + | − |
| 931 | 1 | sugarcane | 6 | + | − |
| 3107 | 1 | corn | 6 | + | − |
| 3111 | 1 | *Canna* | 6 | + | − |
| XR119 | 1 | *panicla* sugarcane | 7 | + | − |
| XR3 | 1 | sugarcane | 7 | + | − |
| (*P. setariae*) | | | | | |
| ATCC 19882 | 1 | rice | 2 | + | − |
| PS177 | 1 | rice | 7 | + | − |
| (*P. rubrisubalbicans*) | | | | | |
| XR105, 106 | 2 | sugarcane | 7 | + | − |
| *A. avenae* subsp. *citrulli* (*P. pseudoalcaligenes* subsp. *citrulli*) | | | | | |
| HIB, H17, B164 | 3 | watermelon | 8 | + | + |
| 1214, wwG, Mie3 | 3 | watermelon | 8 | + | + |
| ATCC 29625 | 1 | watermelon | 2 | + | + |
| 9217, 8408 | 2 | watermelon | 9 | + | + |
| 2576, 2578 | 2 | watermelon | 8 | + | + |
| *A. avenae* subsp. *cattleyae* | | | | | |
| ATCC 33619 | 1 | orchid | 2 | + | − |
| PC, 107, 112, 145 | 3 | orchid | 7 | − | − |
| *A. avenae* subsp. *konjaci* (*P. pseudoalcaligenes* subsp. *konjaci*) *Amorphophallus rivieri* | | | | | |
| ATCC 3399 | 1 | Konjac | 2 | − | − |
| *A. facilis* (*P. facilis*) | | | | | |
| ATCC11228 | 1 | soil | 2 | − | − |
| *Burkholderia caryophylli* (*P. caryophylli*) | | | | | |
| PC131 | 1 | carnation | 7 | − | − |
| *B. cepacia* (*P. cepacia*) | | | | | |
| PC22, PC142 | 2 | onion | 7 | − | − |
| *B. gladioli* pv. *allicola* (*P. allicola*) | | | | | |
| PA7 | 2 | onion | 7 | − | − |
| PA16 | 1 | gladioli | 7 | − | − |
| *B. gladioli* pv. *gladioli* | | | | | |
| ATCC 25417 | 1 | gladioli | 2 | − | − |
| *B. glumae* (*P. glumae*) | | | | | |
| COG1–4 | 4 | rice | 1 | − | − |
| ATCC 33617 | 1 | rice | 2 | − | − |
| *P. fuscovaginae* | | | | | |
| Fed1259–3 IR VM | 1 | rice | 10 | − | − |
| *P. oryzicola* | | | | | |
| PO101 | 1 | rice | 7 | − | − |
| *P. syringae* pv. *syringae* | | | | | |
| Chi131–3 | 1 | rice | 1 | − | − |
| B728a | 1 | beans | 11 | − | − |

TABLE 1-continued

Species and strains and results of PCR with primers
SEQ ID NOS: 1 & 2 of *Acidovorax avenae* subsp. *avenae*
and with the primers SEQ ID NOS: 3 & 4 of *A. avenae* subsp. *citrulli*

| Bacterial strains | No. | Host | Source[a] | PCR-Amplification SEQ ID NOS: 1 and 2[b] | PCR-Amplification SEQ ID NOS: 3 and 4[c] |
|---|---|---|---|---|---|
| *Xanthomonas oryzae* pv. *oryzae* | | | | | |
| CXO105, 211, 315 | 3 | rice | 1 | − | − |
| ATCC 35932 | 1 | rice | 2 | − | − |
| *X. oryzae* pv. *oryzicola* | | | | | |
| P501 | 1 | rice | 13 | − | − |
| ATCC 40972 | 1 | rice | 2 | − | − |
| *Pantoea herbicola* | | | | | |
| CEh1 | 1 | rice | 1 | − | − |
| ATCC 23375 | 1 | *Milletia japonica* | 2 | − | − |
| *P. syringae* pv. *phaseolicola* | | | | | |
| C199 | 1 | beans | 12 | − | − |
| *P. fluorescens* | | | | | |
| ATCC 13525 | 1 | | 2 | − | − |
| Other bacteria | | | | | |
| UPL1–6, UXL 1–7 | 13 | rice seeds | 14 | − | − |
| UWPL1–8, UWB 1–8 | 14 | watermelon seeds | 14 | − | − |

[a]1, W. Y. Song, Dept. Agric. Biology, Chonbuk National University, Chonju, Korea; 2, ATCC, American Type Culture Collection, Rockville, MD, USA; 3, ICPPB, International Collection of Plant Pathogenic Bacteria, USDA, Frederick, MD, USA; 4, L. E. Claflin, Dept. Plant Pathology, KSU, Manhatten, KS, USA; 5, C. Mortensen, Danish Govt. Inst. of Seed Pathology for Developing Countries, Copenhagen, DK; 6, MAFF, Ministry of Agriculture, Forestry and Fisheries of Japan, Tsukuba, Japan; 7, NCPPB, National Collection of Plant Pathogenic Bacteria, Harpenden, UK; 8, P. S. Randhawa, California Seed & Plant Lab., Elverta, California USA; 9, R. Latin, Dept. Plant Path., Purdue, Univ. West Lafayette, IN, USA; 10, F. Correa, CIAT, Cali, Colombia; 11, S. Hutchenson, Plant Biology Dept, Univ. Maryland, College Park, MD, USA; 12, T. Mew, IRRI, Manila, Philippines; 13, N. W. Schaad, ARS/USDA, Frederick, MD, USA; 14, this study.
[b]Positive result means presence of 550 bp band and negative means no visible band in ethidium bromide stained agarose gel.
[c]Positive result means presence of 450 bp band and negative means no visible band in ethidium bromide stained agarose gel.

In brief, the DNA amplification process is carried out by (a) providing a biological sample comprising bacterial cells or extracted DNA for standard PCR or cells amplified by growing on an agar medium for BIO-PCR; (b) amplifying a target sequence of the DNA to provide DNA amplification products carrying the selected target DNA sequence; and (c) detecting the presence of the DNA amplification products as an indication of the presence of *A. avenae*.

The biological sample may either be bacteria cells or extracted genomic DNA. The biological sample may be a test sample suspected of containing bacterial cells, and thus the DNA of the bacterial cells, or a test sample containing extracted DNA.

The BIO-PCR method, disclosed in U.S. patent application Ser. No. 08/344,085, herein incorporated by reference, combines biological preamplification (enrichment) of the PCR target organism with enzymatic amplification of the PCR target. Briefly, the advantages of the BIO-PCR method, over those of the standard PCR assay, include the detection of live cells only, a 100–1000 fold increase in sensitivity, and elimination of PCR inhibitors associated with plant samples thereby eliminating false negatives. Sample processing can be further simplified by directly processing the samples comprising the expanded cells without further DNA extraction. However, even if a DNA extraction step is included, an advantage of the BIO-PCR methodology is that the DNA is extracted from a growing, viable population of cells or microorganisms. The enhanced sensitivity of the BIO-PCR method is particularly valuable, for example, in those screening situations where the monetary value of a particular seed type is high, and thus it is desirable to test the smallest quantity of seeds possible, and where among trading partners, there is zero tolerance or quarantine for contaminating pathogens.

The preamplification step involves a plating step on an agar or liquid growth medium prior to PCR analysis. A single cell per 0.1 ml can be detected because the single cell multiplies into a tiny colony containing over 10,000 cells on the agar medium. Bacteria are recovered from suspect seeds of rice and watermelon by first soaking 1000–2000 seeds in 0.02% TWEEN 20 solution (ratio of 5 ml/g) for 4 hours at 40° C., pipetting aliquots of 0.1 ml of the bacterial extracts either onto plates of general purpose agar media, such as, KB or nutrient agar (NA), or onto a semiselective medium such as EBB or SPL, described below, and then cloning. For BIO-PCR, each of five plates is washed three times with 1.0 ml of water and the resulting 14–15 ml of wash solution can be used directly for PCR-amplification or the DNA extracted using standard DNA extraction kits.

Similarly, for standard PCR, either the DNA can be extracted or intact cells used. Since only pinpoint-size colonies are needed, incubation time ranges from only 10–15 hr for fast growing bacteria to 24–48 hrs for most plant pathogenic bacteria, depending on the media. An incubation of 24 hrs at 37° C. is used for *A. avenae*. Since the incubation time is short, few other bacterial colonies are present.

EBB medium is a preferred, semiselective medium to use for the preamplification step for enrichment of *A. avenae* subsp. *avenae* and *A. avenae* subsp. *citrulli*. The protocol for preparing the EBB Medium is as follows:

(1) Mix, per liter:

| | | |
|---|---|---|
| $NH_4PO_4$ | 1.0 | g |
| $MgSO_4 \cdot 7\ H_2O$ | 0.2 | g |
| KCl | 0.2 | g |
| Yeast Extract | 0.3 | g |
| Boric acid | 0.5 | g |
| Brilliant blue R (10 mg/ml Stock) | 1.0 | ml |
| Bromcreosol purple (15 mg/ml Stock) | 0.6 | ml |
| Agar | 16.0 | g |

(2) Autoclave and add, per liter: 10.0 ml 95% ethanol 1.0 ml Cycloheximide (200 mg/ml 95% ethanol Stock)

(3) Adjust pH carefully to 5.2 using 0.2 M HCl just before autoclaving. (If the pH falls below 5.0, do not use NaOH to readjust to 5.2 as NaOH will neutralize brilliant blue R.)

In the preferred method, the enzymatic amplification of the DNA sequence is by polymerase chain reaction (PCR), as described in U.S. Pat. No. 4,683,202 to Mullis, herein incorporated by reference. In brief, the DNA sequence is amplified by reaction with at least one oligonucleotide primer or pair of oligonucleotide primers that hybridize to the target sequence or a flanking sequence of the target sequence and a DNA polymerase to extend the primer(s) to amplify the target sequence. The amplification cycle is repeated to increase the concentration of the target DNA sequence. Amplified products are optionally separated by methods such as agarose gel electrophoresis. The amplified products can be detected by either staining with ethidium bromide or silver stain or by hybridization to a labeled probe, such as in TaqMan PCR which is based on real time hybridization. In an alternative embodiment, at least one probe that hybridizes to the amplified products is labeled with either a biotin moiety and/or a fluorescent moiety. The complexes are then bound to a solid support such as a bead, multiwell plate, dipstick or the like that is coated with streptavidin. The presence of bound hybrids can then be detected using an antibody to the fluorescent tag conjugated to horseradish peroxidase. The enzymatic activity of horseradish peroxidase can be detected with a colored, luminescent, or fluorimetric substrate. Conversion of the substrate to product can be used to detect and/or measure the presence of A. avenae PCR products.

Other methods of PCR using various combination of primers, normally from one to three primers are known to those of skill in the art and are described in Maniatis (1989. *Molecular Cloning: A Laboratory Manual*. Cold Spring Harbor, N.Y.). Those methods include asymmetric PCR, PCR using mismatched or degenerate primers, reverse transcriptase PCR, arbitrarily primed PCR (Welsh et al. 1990. *Nucleic Acids Res.* 18: 7213–7218), or RAPD PCR, IMS-PCR (Islam et al. 1992. *J. Clin. Micro.* 30:2801–2806), multiwell PCR (ELOSA) (Luneberg et al. 1993. *J. Clin. Micro.* 31:1088–1094), and Katz et al. 1993. *Am. J. Vet. Res.* 54:2021–2026). The methods also include amplification using a single primer as described by Judd et al. 1993. *Appl. Env. Microbiol.* 59:1702–1708).

An oligonucleotide primer preferably has a DNA sequence that hybridizes under standard conditions for PCR to a sequence flanking one end of the DNA sequence to be amplified. In the use of a pair of oligonucleotide primers, each of the primers is distinct and has a different DNA sequence. The two distinct primers are directed at specific sequences on opposite strands and together define the segment to be amplified, i.e., they hybridize to sequences at either end of the target sequence. Design of primers and their characteristics have been described previously. The DNA sequences of the oligonucleotide primers are positive-sense (forward) 5'-GTCGGTGCTMCGACATGG-3' (SEQ ID NO:1), negative sense (reverse) 5'-AGACATCTCCGCTTTCTTTCAA-3' (SEQ ID NO:2), positive sense (forward) 5'-GGAAGAATTCGGTGCTACCC-3' (SEQ ID NO:3), negative sense (reverse) 5'-TCGTCATTACTGAATTTCAACA-3' (SEQ ID NO:4), or complements thereof, or mixtures thereof. The primers may also be degenerate primers that hybridize to the target DNA sequence under hybridization conditions for a primer of that size and sequence complementarity.

For the binding and amplification, the biological sample (bacterial cells or extracted DNA) is provided in an aqueous buffer formulated with an effective amount of a divalent cation which is preferably $MgCl_2$, preferably at a concentration of about 0.05–5 mM; an effective amount of DNA polymerase with Taq DNA polymerase being preferred in the form of native purified enzyme or a synthesized form such as AMPLITAQ (Perkin-Elmer), an effective amount of dNTPs as a nucleotide source, including, dATP, dCTP, dGTP, and dTTP, preferably in a saturating concentration, preferably about 200 $\mu$M per dNTP; and an effective amount of one or a pair of oligonucleotide primers. The reaction mixture containing the annealed primer(s) is reacted with a DNA polymerase at about 72° C. to about 94° C. for about 1–10 minutes, to extend the primers to make a complementary strand of the target gene sequence. The cycle is then repeated by denaturing the DNA strands with heat, annealing and extending, preferably for about 25–40 cycles, preferably about 30 cycles.

If designed properly, a single product results. This product is preferably about 450–550-kb in size, whose termini are defined by the oligonucleotide primer(s), and whose length is defined by the distance between the two primers or the length of time of the amplification reaction. The gene sequence then serves as a template for the next amplification cycle.

The amplified DNA product is optionally separated from the reaction mixture and then analyzed. The amplified gene sequence may be visualized, for example, by electrophoresis in an agarose or polyacrylamide gel or by other like techniques, known and used in the art.

The amplified gene sequence may be directly or indirectly labeled by incorporation of an appropriate visualizing label, as for example, a radioactive, colorimetric, fluorometric or luminescent signal, or the like. In addition, the gel may be stained during or after electrophoresis with a visualizing dye such as ethidium bromide or silver stain wherein the resulting bands by be visualized under ultraviolet light.

To prove the identity of the amplified DNA product, a Southern blot assay should be conducted. The amplified products are separated by electrophoresis on a polyacrylamide or agarose gel, transferred to a membrane such as a nitrocellulose or nylon membrane, reacted with an oligonucleotide probe, and stained as above. The amplified products may also be detected by reverse blotting hybridization (dot blot) in which an oligonucleotide probe specific to the gene sequence is adhered to a nitrocellulose or polyvinylchloride (PVC) support such as a multi-well plate, and then the sample containing labeled amplified product is added, reacted, washed to remove unbound substance, and a labeled amplified product attached to the probe or the gene sequence imaged by standard methods.

A major advantage of TaqMan PCR is that the technology is based on hybridization; therefore, a Southern blot assay is not needed. The DNA sequences of the oligonucleotide primers for TaqMan PCR are positive-sense (forward) 5'-CCTCCA CCAACCAATACGCT-3' (SEQ ID NO: 5), negative sense (reverse) 5'-TCGTCATTACTG AATTTCAACA-3' (SEQ ID NO:4), and negative sense (reverse) 5'-CATGCTCTTAGT CACTTGACCCTA-3' (SEQ ID NO:6), or complements thereof, or mixtures thereof. The DNA sequence of the probe utilized in the TaqMan PCR is 5'-CGGTAGGGCGAA GAAACCAACACC-3' (SEQ ID NO:7).

The detection of amplified gene product in the sample is evidence of the presence of *A. avenae* subspecies in the biological sample. When combined with BIO-PCR, the method is useful in diagnosing presence of viable cells of *A. avenae*. One set of primers, primers identified by SEQ ID NO:1 and SEQ ID NO:2, is useful in a detection assay to identify that *A. avenae* is present in a sample; specifically, that any one or all of the subspecies, *A. avenae* subsp. *avenae, A. avenae* subsp. *cattleyae*, or *A. avenae* subsp. *citrulli*, are present. The primer set comprising SEQ ID NO:1 and SEQ ID NO:2 cannot distinguish the subspecies avenae, *cattleyae*, and *citrulli*; however, the primer set identified by SEQ ID NOS: 1 and 2, can be used to screen for the presence of any or all of these organisms. The primer set comprising SEQ ID NO:3 and SEQ ID NO:4 distinguishes *A. avenae* subsp. *citrulli* from *A. avenae* subsp. *avenae* and *cattleyae*. When the advantages of the BIO-PCR are combined with the specificity of SEQ ID NO:3 and SEQ ID NO:4 for *A. avenae* subsp. *citrulli*, the sensitivity and specificity for detecting the pathogen responsible for watermelon fruit blotch is further enhanced.

Detection utilizing the BIO-PCR method is enhanced still further when combined with the TaqMan detection system. When the primer set comprising SEQ ID NO:5 with either SEQ ID NO:4 or SEQ ID NO:6 is utilized in a combined BIO-PCR and TaqMan method, such methodology results in the detection of as few as 2 cfu/ml. Thus, there is no loss of sensitivity as compared to BIO-PCR and Southern analysis. Two important advantages of the TaqMan system are (1) that measurement of real-time hybridization is rapid and (2) that the hybridization product is the definitive, irrefutable product of the polymerization chain reaction. Further, the methodology involved in the assay process makes possible the handling of large numbers of samples efficiently and without cross-contamination and is therefore adaptable for robotic sampling. The advantages of rapid, conclusive data together with labor and cost efficiency make the combination BIO-PCR and TaqMan detection system utilizing the specific primers of the invention a highly beneficial system for monitoring seed pathogens, especially in those circumstances where seed screening results have major commercial and trade consequences.

The screening for *A. avenae* subsp. *avenae, cattleyae*, and *citrulli*, using the primer set consisting of SEQ ID NO:1 and SEQ ID NO:2, can be followed by a detection assay utilizing the primer set consisting of SEQ ID NO:3 and SEQ ID NO:4 in order to specifically detect the presence of *A. avenae* subsp. *citrulli*. Furthermore, in such screening assays, where a detection assay utilizing a primer set identified by SEQ ID NO:1 and SEQ ID NO:2 is followed by a detection assay utilizing a primer set identified by SEQ ID NO:3 and SEQ ID NO:4, a negative result in the detection assay utilizing the primer set consisting of SEQ ID NO:3 and SEQ ID NO:4 is indicative of either or both *A. avenae* subsp. *avenae* or *cattleyae* being present and that *A. avenae* subsp. *citrulli* is not present. Similarly, where a detection assay utilizing a primer set identified by SEQ ID NO:1 and SEQ ID NO:2 is followed by a TaqMan detection assay utilizing the primer set comprising SEQ ID NO:5 together with either SEQ ID NO:4 or SEQ ID NO:6, a negative result in the second detection assay, utilizing SEQ ID NO:5 together with SEQ ID NO:4 or 6, is indicative of either or both *A. avenae* subsp. avenaeor *cattleyae* being present and that *A. avenae* subsp. *citrulli* is not present.

The Detection of the Rice Strains of *A. avenae* subsp. *avenae*

The primers identified as SEQ ID NO:10, SEQ ID NO:11, and SEQ ID NO:12 and the primer sets comprising the primer pairs SEQ ID NOs:10 and 12 and SEQ ID NOs:11 and 12 are useful in an assay to detect the presence of the rice strains of *A. avenae* subsp. *avenae* in a sample.

Genomic DNA was extracted from cultures of *A. avenae* subsp. *avenae*: a rice strain Caa4, a corn strain ATCC19860, and two forage strains MAFF301027 from wheatgrass and MAFF301030 from rescuegrass. The amplification of the ISR was performed using known primers R16-1 and R23-2R and the method described by Kim et al., supra. The amplified product was electrophoresed in a 2% Metaphore gel (FMA BioProducts, Rockland, Md.). The resulting target DNA band was excised from the gel and purified by using QIAquick gel extraction kit following the suppliers recommendations (QIAGEN, USA). The sequencing of the purified full length 950-bp product was performed by the dideoxy-chain termination method using ABI PRISM 310 Genetic Analyzer and Dye Terminator Cycle Sequencing Core Kit (Perkin Elmer, Foster City, Calif.) following the manufacturer's protocol. From the ISR sequences, candidate primers were selected using the program OLIGO (National Biosciences, Hamel, Minn.). Oligonucleotide primers SEQ ID NOs: 10, 11, and 12 from the ISR sequence of *A. avenae* subsp. sequences were used in the seminested PCR assay. The sequences of the primers were as follows: 5'-GTCATCCTCCACCAACCAAG-3' (SEQ ID NO:10); 5'-AGATGCCCTGCGGTAGGGCG-3' (SEQ ID NO:11); and 5'-AGAACAATTCGTCATTACTGAAC-3' (SEQ ID NO:12). The first PCR step, performed with primers SEQ ID NO:10 and SEQ ID NO:12, amplified a fragment having a size of 262 bp, while the size of the final PCR product obtained with primers SEQ ID NO:11 and SEQ ID NO:12 was 241 bp. The primers were synthesized commercially by Bioneer Corporation (Chungwon, Chungbuk, Korea).

The PCR was carried out by performing three kinds of experiments. First, boiled cultures of strains of Acidovorax species, other bacterial rice or plant-pathogenic species, and other unidentified seedborne bacteria were amplified to test the specificity of the PCR primers. Second, the sensitivity of the seminested PCR assay was determined by amplifying a serially diluted culture of *A. avenae* subsp. *avenae*. Third, the sensitivity for detecting *A. avenae* subsp. *avenae* cells in inoculated rice seed samples was determined.

Cells of 76 strains of *A. avenae* subsp. *avenae*, 10 strains of *A. avenae* subsp. *citrulli*, two of *A. avenae* subsp. *cattleyae*, two strains of *A. konjaci*, and a single strain of *A. facilis* (type strain of the genus), 24 strains of other known rice pathogenic bacteria, 11 strains of other outgroup species, and 29 isolates of unknown non-pathogenic bacteria from rice seeds were used to screen primers. The specificity of each set of primers is illustrated in Table 2, below.

TABLE 2

Species and strains used in this study and results of PCR with primer sets SEQ ID NOs: 10 and 12 and SEQ ID NOs: 11 and 12 of *A. avenae* subsp. *avenae*

| Bacterial strains | Host | Source[a] | PCR-Amplification[b] SEQ ID NOS: 10 and 12[b] | SEQ ID NOS: 11 and 12[c] |
|---|---|---|---|---|
| *Acidovorax avenae* subsp. *avenae* | | | | |
| COA1–3, Caa1–12, 30–43 | Rice | 1 | + | + |
| 19882 | Rice | 2 | + | + |
| 301502–301511 | Rice | 3 | + | + |
| 311056–311058 | Rice | 3 | + | + |
| 39461g, 39462c | Rice | 4 | + | + |
| Nepal | Rice | 4 | + | + |
| 39123a, 39459–39463 | Rice | 4 | + | + |
| Acc40560-6, Acc40582-A1 | Rice | 4 | + | + |
| 19860 | Corn | 2 | – | – |
| 3107 | Corn | 5 | – | – |

TABLE 2-continued

Species and strains used in this study and results of PCR with primer sets SEQ ID NOs: 10 and 12 and SEQ ID NOs: 11 and 12 of *A. avenae* subsp. *avenae*

| Bacterial strains | Host | Source[a] | PCR-Amplification[b] SEQ ID NOS: 10 and 12[b] | SEQ ID NOS: 11 and 12[c] |
|---|---|---|---|---|
| 19307 | Sugarcane | 2 | – | – |
| 931 | Sugarcane | 5 | – | – |
| 3111 | Canna sp. | 5 | – | – |
| 3403PAv | Vaseygrass | 6 | – | – |
| 301036 | Teosinte | 3 | – | – |
| 3431PAv | Millet | 6 | – | – |
| 301027 | Wheatgrass | 3 | – | – |
| 301030 | Rescue grass | 3 | – | – |
| 301141 | Finger millet | 3 | – | – |
| CAa301Cg-311Cg | Finger millet | 1 | – | – |
| 301609 | Dallis grass | 3 | – | – |
| *A. avenae* subsp. *cattleyae* | | | | |
| 301576 | Phalaenopsis sp. | 3 | – | – |
| 33619 | Orchid | 2 | – | – |
| *A. avenae* subsp. *citrulli* | | | | |
| 29625 | Watermelon | 2 | – | – |
| HIB, Hi7, B164, 1214, WWG, Mie3, 2576 | Watermelon | 7 | – | – |
| 9217, 8408 | Watermelon | 8 | – | – |
| *A. facilis* | | | | |
| 11228 | Soil | 2 | – | – |
| *A. konjaci* | | | | |
| 33996 | Konjac | 2 | – | – |
| 301465 | Konjac | 3 | – | – |
| *Varivorax paraxoxus* | | | | |
| 17713 | Soil | 2 | – | – |
| Other rice pathogenic species (24)[c] | Rice | 1–4, 9–12 | – | – |
| Other outgroup species (11)[d] | | 2, 3, 10, 13 | – | – |
| Seed-extracted bacteria: | | | | |
| Nonfluorescent Pseudomonas spp. (8) | Rice | 14 | – | – |
| Fluorescent Pseudomonas spp. (6) | Rice | 14 | – | – |
| Erwinia spp. (3) | Rice | 14 | – | – |
| Xanthomonas-like bacteria (7) | Rice | 14 | – | – |
| Unidentified isolates (5) | Rice | 14 | – | – |

[a]1, W. Y. Song, Dept. Agric. Biology, Chonbuk National University, Chonju, Korea; 2, ATCC, American Type Culture Collection, Rockville, MD, USA; 3, MAFF, Ministry of Agriculture, Forestry and Fisheries of Japan, Tsukuba, Japan; 4, C. Mortensen, Danish Govt. Inst. of Seed Pathology for Developing Countries, Copenhagen, DK; 5, NCPPB, National Collection of Plant Pathogenic Bacteria, Harpenden, UK; 6, L. E. Claflin, Dept. Plant Pathology, KSU, Manhatten, KS, USA; 7, P. S. Randhawa, California Seed & Plant Lab., Elverta, California USA; 8, R. Latin, Dept. Plant Path., Purdue, Univ. West Lafayette, IN, USA; 9, F. Correa, CIAT, Cali, Colombia; 10, ICPPB, International Collection of Plant Pathogenic Bacteria, USDA, Frederick, MD, USA; 11, T. Mew, IRRI, Manila, Philippines; and 12, S. Hutchenson, Plant Biology Dept, Univ. Maryland, College Park, MD, USA; and 14, this study.
[b]Positive result means presence of 262 bp band in first PCR step with primers SEQ ID NOS: 10 and 12 and 241 bp in second seminested PCR step with primers SEQ ID NOS: 11 and 12. Negative means no visible band in ethidium bromide stained agarose gel.
[c]Species and strain (origin) of other rice pathogenic bacteria: *Burkholderia glumae* COG1–3 (1), 301095–301099 (4) & 33617 (2); *B. plantarii* 301723 (3); *Pseudomonas fuscovaginae* 301177 (3) & Fed1259–3 (10); *P. marginalis* pv. *marginalis* 301173 (3); *P. oryzicola* PO101 (11); *P. syringae* pv. *syringae* Chil31–3 (10); *Xanthomonas oryzae* pv. *oryzae* CXO150, 211 & 315 (1) and 35932 (2); *X.o.* pv. *oryzicola* P501 (12) and 40972 (2); *Pantoea anantis* 2101 (14); and *P. herbicola* CEh1 (1) and 23375 (2).
[d]Species and strain (origin) of other outgroup bacteria: *Burkholderia andropogonis* 33061 (2); *B. caryophylli* 25418 (2); *B. cepacia* 25416 (2); *B. gladioli* pv. *allicola* PA7 & PA16 (11) and 19302 (2); *B. gladioli* pv. *gladioli* 10248 & 25417 (2); *P. fluorescens* 13525 (2); *P. syringae* pv. *aptata* 301008 (3); and *P. syringae* pv. *syringae* (14).

Diagnostic BIO-PCR-based assays utilize sample enrichment to elevate low numbers of target bacteria to enhance detection limits and to escape the interference of inhibitors or other ubiquitous seedborne bacteria in PCR-based seed testing. The use of a selective enrichment medium results in the suppression of most of the accompanying microflora while allowing a direct recovery of the pathogen before PCR amplification. Several selective or differential media have been described for the classical isolation of various host-originated *A. avenae* subspecies (Kadota, supra; Summer et al. (1977. *Phytopath.* 67:1113–1118); and Alvarez et al. 1989. *Int. Rice research Newsletter* 14: 27–28). However, no medium has been proven to be effective for enhancing identification of the rice strains of *A. avenae* subsp. *avenae* from rice seed. Plating seed extracts on sorbitol-neutral red agar (SNR) or *Pseudomonas avenae* selective medium (PASM) has been used previously to assay rice samples for *A. avenae* subsp. *avenae*, but with limited success.

Preliminary evaluation of some media previously reported to be selective for *A. avenae* subsp. *avenae* either resulted in poor recovery or failed to adequately inhibit the growth of saprophytic flora from rice seeds. From the results of GN Biolog test for rice strains of *A. avenae* subsp. *avenae*, several carbon and nitrogen sources were compared for having the effect of efficient recovery of *A. avenae* subsp. *avenae* and reduced recovery of other rice seedborne bacteria. D-sorbitol and L-pyroglutamic acid were selected as primary carbon and nitrogen sources, respectively, for the new selective medium. All eight strains of *A. avenae* subsp. *avenae* readily utilize both substrates. D-Sorbitol has been used as the carbon source in SNR medium, the medium originally used to isolate *A. avenae* subsp. *avenae*, the causal agent of bacterial leaf blight of corn (Summer et al, supra). We found that SNR worked well with corn strains, but not with rice strains. Furthermore, it failed to inhibit large numbers of saprophytes from rice seeds. The combination of ampicillin and vancomycin does not affect the growth of *A. avenae* subsp. *avenae* but inhibits most seedborne contaminants commonly found in rice seeds as well as other rice pathogenic bacteria tested. The final selective enrichment medium is designated sorbitol-pyroglutamic acid (SPL). To enhance the colony differentiation between *A. avenae* subsp.

*avenae* and other bacteria from rice seeds, Tween 80 for lipid hydrolysis, Victoria Blue for coloring lipase, bromthymol blue for differentiating colonies, and agar were added to the newly designed SPL medium in plating procedures.

Assays of rice seeds obtained from field harvested seeds show that all seeds are not necessarily contaminated with *A. avenae* subsp. *avenae*, and that even among the contaminated seeds, the level of contamination varies widely. The major advantage of this selective enrichment medium over NBY, SNR, or PASM medium is a significant reduction in growth of saprophytes in the medium without inhibition of *A. avenae* subsp. avenaegrowth. Therefore, SPL medium has proven to be very effective for isolating *A. avenae* subsp. *avenae* from rice seeds. This new selective enrichment medium SPL is well suited for use in detecting *A. avenae* subsp. *avenae* in discolored seeds and seeds that appear to be healthy. Also, SPL medium shows potential as an epidemiological tool for quantitatively monitoring populations of *A. avenae* subsp. *avenae*. By using SPL medium, which eliminates many bacteria which commonly appear on general medium, one can more accurately monitor inoculum populations in rice seeds. Due to its high selectivity, SPL is useful for the detection of *A. avenae* subsp. *avenae* in routine BIO-PCR-based monitoring of rice seed samples.

A seminested BIO-PCR technique based on amplification of the ISR sequence between 16S and 23S and a liquid enrichment step is used with a simple DNA extraction procedure to detect small numbers of *A. avenae* subsp. *avenae* in commercial untreated rice seed. Use of seminested primers increases the sensitivity and specificity of the assay. Any nonspecific amplicons produced during the first PCR step should not have functioned as target DNA during the second PCR step due to a lack of complementarity with the inner primer sequence, thus making routine confirmation of the product by a hybridization procedure less of a necessity (Arnheim et al. 1992. *Ann. Rev. Biochem.* 61:2105–2114). Use of our primers in a TaqMan system eliminates the need for Southern analysis.

Methods which could directly detect *A. avenae* subsp. *avenae* cells in environmental or seed samples without a 12 hr enrichment step would make the assay more rapid. However, major obstacles to the development of more rapid methods include the presence of PCR inhibitors, the small numbers of target cells, and the high numbers of ubiquitous seedborne bacteria. Although dilution of a sample is a simple and useful method to reduce the effect of the inhibitors, there is a risk of diluting out *A. avenae* subsp. *avenae* contamination in the samples. Furthermore, ubiquitous background organisms which are often numerically dominant in rice seed samples often overgrow the target bacterium, interfering with generating a specific product, and occasionally making interpretation of the PCR results difficult. A practical PCR-based seed assay which can overcome these obstacles becomes advantageous for the routine assay of *A. avenae* subsp. *avenae* in rice seeds. Thus, a selective enrichment procedure combined with a simple cell-lysis step prior to the PCR is preferred.

In conclusion, the methods described herein are useful and specific for routine detection of *A. avenae* subsp. *avenae*, *A. avenae* subsp. *citrulli*, and specific strains of *A. avenae* subsp. *avenae* pathogenic to rice. The described techniques are useful for environmental samples having high levels of microbiological contamination or humic matter, as well as for seed samples containing high levels of background flora. This liquid enrichment-based BIO-PCR assay can detect very small numbers of *A. avenae* subsp. *avenae* even in the presence of high numbers of saprophytes. The assay can be completed in 2 days, which is considerably shorter than traditional growing-on and agar media techniques.

The primers and amplification method can further be useful for evaluating and monitoring the efficacy of any treatments utilized to eradicate pathogenic *A. avenae* subspecies from seeds. In this method, biological samples are obtained from seeds prior to treatment and from seeds which have undergone treatment with a protocol such as hot water or household bleach, designed to eradicate the bacterium. In addition, biological samples can be obtained from seeds at several time intervals during treatment. Specific DNA amplification products of *A. avenae* are easily analyzed. Results from samples obtained prior, during and after treatment are compared in order to determine efficacy of the treatment protocol.

Similarly, the novel primers and methods are very useful for epidemiology and host-pathogen studies. A further advantage of using BIO-PCR is that quantitative data on viable pathogen populations can be obtained by dilution-end-point analysis if samples are not heavily contaminated with saprophytes in those instances when quantification of propagules would be desirable. The existence of a combined selective enrichment PCR-based method (BIO-PCR) to identify *A. avenae* subsp. *avenae*, rice specific strains of *A. avenae* subsp. *avenae*, and *A. avenae* subsp. *citrulli* represents a valuable tool for monitoring natural disease spread, tracking specific seedborne bacteria in field studies, and detecting the presence of the bacterium in imported seed lots entering *A. avenae* free areas.

EXAMPLES

Example 1

Bacterial Cultures

The strains and source of Acidovorax and other bacteria used in this study are shown in Tables 1 and 2. Cultures were maintained on yeast extract-dextrose calcium carbonate (YDC) or King et al.'s medium B (KB) agars at room temperature and stored at −85° C. Colony morphology of *A. avenae* strains were checked on YDC and KB media and accumulation of poly-β-hydroxybutyrate determined as described (Schaad. 1988, supra). Colonies of all strains received as *A. avenae* subsp. *avenae* (including *P. rubrilineans*, *P. setariae*, and *P. rubrisubalbicans*) were non-fluorescent on KB medium, round convex morphology and tan in color on YDC medium. Colonies of *A. avenae* subsp. *citrulli*, *A. konjaci*, and ATCC strain 33619 of subsp. *cattleyae* had colonies indistinguishable from *A. avenae* subsp. *avenae*. All these strains were positive for Poly-β-hydroxybutyrate on nile blue medium (Pierce et al. 1994. *Plant Dis.* 78:683–685). In contrast, morphologies of strains PC107, 112, and 145 of subsp. *cattleyae* were very different and these strains did not accumulate Poly-β-hydroxybutyrate. We therefore concluded that these cultures were contaminants and not subsp. *cattleyae*.

Final identity of all *A. avenae* subsp. *avenae* strains was confirmed by inoculating oat and corn seedlings, as described (Schaad et al. 1975, supra). The identity of all strains of *A. avenae* subsp. *citrulli* were confirmed by inoculating watermelon seedlings (Schaad et al. 1978, supra); identity of all rice strains of *A. avenae* subsp. *avenae* was confirmed by inoculating rice seedlings.

Example 2

Preparation of Seed Samples Prior to PCR

For seed samples screened as on Table 1: Bacteria were extracted from healthy seeds of rice and watermelon, by soaking 1000–2000 seeds in 0.02% Tween 20 solution (ratio of 5 ml/g) for 4 hr at 40° C. Aliquots of 100 μl were pipetted onto each of ten plates of KB, nutrient agar (NA), YDC, or a semiselective agar medium such as neutral red semiselective medium (Schaad. 1988. Laboratory Guide for Identification of Plant Pathogenic Bacteria, 2nd Ed., APS Press, St. Paul, Minn.) for *A. avenae* subsp. *avenae* or EBB for *A. avenae* subsp. *citrulli*, and spread with a L-shaped glass rod. After 48 hrs incubation at 36° C., five plates were washed three times with 1.0 ml of 10 mM Tris-HCl solution (pH 7.4) for BIO-PCR as described (Schaad et al. 1995, supra) and the sample archived at −20° C. The remaining five plates were read for visible suspect colonies after three and four days. Suspect colonies were cloned and stored on YDC slants at room temperature for pathogenicity tests. Short term storage should be at room temperature as these bacteria do not survive well at 2–40° C.

For seed samples to be screened with primer set SEQ ID NO:10 and 12 and primer set SEQ ID NO:11 and 12, eleven local (Chonbuk, Korea) seed samples were collected from 1993 to 1999, transported to the laboratory at ambient temperature, and kept at 40° C. (Table 2). Standard dilution plate count procedures were used to enumerate total bacteria and *A. avenae* subsp. *avenae* .

Seed samples were prepared by using the method described below. The analysis was performed with and without overnight enrichment. Ten 30 g aliquots of each seed sample soaked in buffer overnight were inoculated with *A. avenae* subsp. *avenae*. Five of these aliquots were analyzed after a short pelletting procedure, while the third aliquot was subjected to overnight enrichment in liquid medium.

Example 3
Development of Selective Enrichment Liquid Medium

To define components of the basal liquid enrichment medium to enhance the selective growth of rice and corn strains of *A. avenae* subsp. *avenae*, carbon and nitrogen sources for growth of *A. avenae* subsp. *avenae* were screened by using Biolog GN microplates (Biolog, Hayward, Calif.). Based on these screening results, several candidate compounds were selected. The utilization of each selected carbon and nitrogen compound was determined by using a defined liquid medium (0.5 g of $K_2HPO_4$, 3.0 g of $Na_2HPO_4$, 3.0 g of $FeSO_4.7H_2O$ per liter) with each candidate combination of a 0.2% carbon and a 0.02% nitrogen source. The optimal combination was selected by comparing the recovery of *A. avenae* subsp. *avenae* and the selectivity of each liquid medium. The recovery and selectivity were compared by dilution plating of liquid cultures onto KB medium and counting CFU of *A. avenae* subsp. *avenae* and/or other bacteria after 2 day-incubation at 28° C. D-sorbitol and L-pyroglutamic acid were found to be the most suitable among all the compounds tested as a carbon and nitrogen source by comparing the recovery efficiency and selectivity to *A. avenae* subsp. *avenae* .

The final basal medium contained D-sorbitol and L-pyroglutamic acid as the carbon and nitrogen sources, respectively. This basal medium was used for selecting inhibitors of other seedborne or pathogenic bacteria of rice. To make the basal medium more selective for *A. avenae* subsp. *avenae*, candidate inhibitors for the selective inhibition of other seedborne saprophytic bacteria and other reported bacterial pathogens of rice were screened. Two rice strains, Caa4 and MAFF301506, and one corn strain, ATCC19860, were cultured in liquid nutrient broth-yeast extract (NBY) medium for 24 hours at 28° C. The concentration of bacterial suspension was adjusted to approximately $1\times10^5$ CFU/ml and the bacterial suspension sprayed onto the surface of basal agar medium. After 20 min, individual 20 μl-absorbable paper discs were dipped into candidate inhibitor solutions. Discs containing each inhibitor were placed on the agar with sterile forceps and gently pressed down to ensure contact. After incubating the plates overnight at 28° C., the diameter of the inhibition zone was measured. Compounds that failed to inhibit the growth of *A. avenae* subsp. *avenae* around the paper disc on the basal agar medium were selected for further screening.

From the results of the paper disc screening, ampicillin and vancomycin were selected as candidates for further selectivity testing. These inhibitors were added to the basal medium containing D-sorbitol and L-pyroglutamic acid and further analyzed for their ability to inhibit saprophytic bacteria without reducing the growth of *A. avenae* subsp. *avenae* in rice seed extracts. To determine the optimum concentration of ampicillin and vancomycin, different concentrations of each inhibitor were tested by comparing recovery efficiency and selectivity for *A. avenae* subsp. *avenae* strains. Eight strains (CAa4–CAa6, MAFF301502–MAFF301504, ATCC19882, and ATCC19860) of *A. avenae* subsp. *avenae* were used to evaluate the recovery efficiency of the final liquid medium. Ampicillin and vancomycin at 150 μg/ml and 25 μg/ml, respectively, suppressed the growth of most saprophytic bacteria from rice seed extracts or other rice pathogenic bacteria tested without inhibiting the growth of *A. avenae* subsp. *avenae*. The final selective enrichment medium, designated sorbitol-pyroglutamic acid (SPL) broth medium, contained 0.5 g of $K_2HPO_4$, 3.0 g of $Na_2HPO_4$, 3.0 g $FeSO_4.7H_2O$, 2.0 g of D-sorbitol, and 0.2 g of L-pyroglutamic acid per liter. The pH of the medium was adjusted to 7.4 before autoclaving. After autoclaving, 150.0 mg of ampicillin and 25.0 mg of vancomycin were added.

The recoveries of the 8 strains of *A. avenae* subsp. *avenae* growing in liquid SPL medium were compared with those on NBY. The SPL medium supported good growth of all 8 strains tested. Recovery efficiencies for the 8 strains of *A. avenae* subsp. avenae ranged from 85.9% to 106.1% with an average of 95.8% compared to that of NBY after 24 hr incubation. Growth of saprophytic bacteria of rice seed extracts as observed in NBY was reduced in SPL medium by 56.2% after 12 hr incubation and by 99.2% after 24 hr incubation. The mean recovery of *A. avenae* subsp. *avenae* from inoculated seeds in SPL, in comparison to NBY, ranged from 78.5% to 120.7% after 15 hr. Because some saprophytic bacteria overgrew *A. avenae* subsp. *avenae* in NBY, the cell numbers of *A. avenae* subsp. *avenae* were uncountable after enrichment for 24 hours. However, because other bacteria in seed extracts grew poorly in liquid SPL, cells of *A. avenae* subsp. *avenae* increased normally.

To determine the recovery of *A. avenae* subsp. *avenae* in spiked seed extracts, 100 ml of SPL medium was seeded with 1.0 ml of seed extract and 1.0 ml of a bacterial suspension previously adjusted to 0.1 at $A600$ and diluted to $10^{-2}$. The mixture was incubated by shaking for 24 at 28° C. The rice seed extracts were prepared by adding 30 g of each rice seed lot to 50 ml of phosphate-buffered saline (PBS, pH 7.6) containing 0.01% Tween 20 and soaking for four hrs at room temperature or overnight at 4° C. The recovery of *A. avenae* subsp. *avenae* and reduction of saprophytic bacteria from rice seed extracts were determined in the final medium. For presumptive identification of *A. avenae* subsp. *avenae* recovered from the spiked samples, PCR with *A. avenae*-specific primers SEQ ID NO:1 and SEQ ID NO:2 was used (Song et al, supra).

A. avenae subsp. avenae was isolated from 25 of the 48 samples harvested from 1993 to 1999 (Table 3). The pathogen was not detected in any of the 5 naturally infected 1993 and 1994 seed lots on SPL agar medium without liquid enrichment. However, it was detected in 2 of the 5 seed samples after a 12 hr enrichment in liquid SPL. Populations of A. avenae subsp. avenae recovered from the two seed lots on SPL agar medium ranged from $3\times10^2$ CFU per ml to $1.27–10^4$ CFU per ml.

for 45 min at room temperature or at 40° C. to remove the coarse particles. After diluting, two 1 ml and 50 μl aliquots of each of the above mixtures were transferred to microcentrifuge tubes and centrifuged at 15,000 rpm for 10 min. The resulting pellets were resuspended in 100 μl of 10 mM Tris-HCl solution (pH 8.0) containing 0.2 mg of proteinase K per ml. After incubating at 50° C. for 1 h, the bacteria were lysed by boiling for 10 min and stored at −20° C. For PCR, each sample was thawed at room temperature and centri-

TABLE 3

Detection of A. avenae subsp. avenae (Aaa) in rice seeds from inoculated and naturally infected seeds with and without enrichment and seminested PCR

| | | | Aaa Detection: No. of Positive Samples[a] | | | | | |
|---|---|---|---|---|---|---|---|---|
| | | | | | With enrichment | | | |
| | No. of Aaa | No. of | Without | | NBY | | SPL | |
| Sample | cells added (CFU/g) | samples analyzed | enrichment Plating | PCR | Plating | BIO-PCR | Plating | BIO-PCR |
| Inoculated Seed Lots[b] | 100–200 | 5 | 4 | 3 | 3 | 3 | 5 | 5 |
| | 10–20 | 5 | 3 | 3 | 2 | 2 | 5 | 5 |
| | 1–2 | 5 | 0 | 0 | 0 | 2 | 2 | 5 |
| | 0 | 5 | 0 | 0 | 0 | 0 | 0 | 0 |
| Naturally Infected Seed Lots | | | | | | | | |
| Dongjin 93, 94 | NA[c] | 5 | 0 | 0 | 0 | 0 | 2 | 2 |
| Dongjin 95, 96, 97 | NA | 18 | 5 | 12 | 3 | 9 | 7 | 15 |
| Dongjin 98, 99 | NA | 12 | 4 | 7 | 2 | 5 | 7 | 9 |
| Dongan 97, 98 | NA | 8 | 3 | 4 | 0 | 4 | 5 | 6 |
| Dongan 99 | NA | 5 | 2 | 3 | 0 | 0 | 4 | 5 |
| Total positive samples | NA | 48 | 14 | 26 | 5 | 18 | 25 | 37 |

[a]The number of samples in which Aaa was detected. Bacterial isolations were performed by plating serial dilutions onto KB and SPL agar plates. Suspect colonies were streaked onto YDC agar and identified by PCR. Seminested PCR amplification was done using primer pairs SEQ ID NOs: 10 and 12 and SEQ ID NOs: 11 and 12.
[b]Seed lots were checked for A. avenae subsp. avenae infection by serial dilution plating and direct PCR using primer pair SEQ ID NOs: 10 and 12. In this sensitivity of recovery test, uninfected seeds were inoculated with A. avenae subsp. avenae adjusted to the indicated cell concentrations.
[c]NA, not applicable

Example 4
Extraction of Genomic DNA and Bacterial Cells from Seeds

For A. avenae subsp. avenae and A. avenae subsp. citrulli:

Cells were grown in Luria-Bertain (LB) liquid medium overnight on a rotary shaker at 30° C. Cell suspensions were centrifuged, suspended in 10 mM Tris-HCl solution (pH 8.0), and adjusted to a concentration of 0.1 OD at A600. Suspensions of cells or single colonies growing on YDC or KB medium were used for PCR-amplification without prior DNA extraction or other sample processing. Genomic DNA was extracted from washed cells, as described (Prosen et al., supra).

For rice strains of A. avenae subsp. avenae:

For analysis without enrichment, five 30 g aliquots of rice seeds from each lot were mixed with 50 ml of PBS solution containing 0.01% Tween 20 and incubated for four hrs at room temperature or overnight at 4° C. on a shaker at 120 rpm. The mixtures were then inoculated with approximately 0, 1~2, 10~20, or 100~200 cells of A. avenae subsp. avenae per g of seed. The mixtures were incubated without shaking fuged at 15,000 rpm for 5 min. A 3 μl, aliquot of the supernatant was added to the PCR mixture resulting in a final volume of 25 μl, and a seminested PCR was performed, as described below.

For analysis of overnight enrichment, each 30 g aliquot was mixed with 50 ml of the extraction buffer, incubated on a shaker, and seeded with the desired number of cells of A. avenae subsp. avenae per g of seed, as described above. The mixture was centrifugated, suspended in the same volume of SPL broth, and incubated on a shaker overnight at 28° C. To remove the course particles, the mixture was incubated at 4° C. for 45 min. Two 100 μl aliquots of the supernatant were transferred to microcentrifuge tubes, centrifuged at 15,000 rpm for 10 min, and stored at −20° C. Seminested PCR was performed as described above. Uninoculated samples were always included as negative controls.

For the analysis of naturally infected seeds, the same extraction and enrichment procedures were applied as described above for analysis with and without enrichment.

Example 5
Design of Primers

The ISR was amplified, as described supra, using primers R16-1 and R23-2R and genomic DNA of *A. avenae* subsp. *avenae* including strains COA1 and Caa4 from rice, ATCC 19860 from corn, MAFF301027 from wheatgrass, MAFF301030 from rescue-grass, and *A. avenae* subsp. *citrulli* strain 29625 from watermelon and melon. The amplified product was electrophoresed in a 2% Metaphore gel (FMA BioProducts, Rockland, Md., USA). The resulting target DNA band was excised from the gel and purified by using the QIAquick gel extraction kit, following the suppliers recommendations (QIAGEN, USA). For *A. avenae* subsp. *avenae*, the DNA of strain COA1 was blunt ended using T4 DNA polymerase, and ligated to plasmid vector pGEM-7Zf(+) (Promega, Madison, Wis., USA), and digested with SmaI, using T4 DNA Ligase. The ligation products were used to transform DH5 competent cells (Life Technologies, MD, USA) according to suppliers recommendations. For *A. avenae* subsp. *citrulli*, the gel-purified product was ligated into pCR2.1 with TA cloning kit (INVITROGEN) following the suppliers protocols.

The amplified full length 950-bp product of ISR of *A. avenae* subsp. *avenae* was cloned into pGEM7f (GIBCO BRL). The resulting clone, pOA3, containing a 950-bp insert of full length ISR, was then sequenced. For *A. avenae* subsp. *citrulli*, the amplified full length 950-bp product of ISR was cloned into pCR2.1 with TA cloning kit (INVITROGEN). The resulting clone, pCIT7, containing a 950-bp insert of full length ISR, was then sequenced.

Chemicals and antibiotics were purchased from Sigma Chemical Co. (St. Louis, Mo.), restriction and DNA modifying enzymes were purchased from Life Technologies (Bethesda, Md.), and all supplies for PCR were purchased from Perkin Elmer (Norwalk, Calif.).

Example 6
Sequence Analysis

The sequencing of the cloned 16S–23S ISR fragment was performed by the dideoxy-chain termination method using ABI PRISM 310 Genetic Analyzer and Dye Terminator Cycle Sequencing Core Kit (Perkin Elmer, Foster City, Calif.) following the manufacturer's protocol (Sanger et al., supra). The sequence of the species-specific ISR fragment of *A. avenae* subsp. *avenae* COAL sequenced was 625 bp (FIG. 1B; Aaa, shaded). The fragment had a GC content of 48.87%, and a single tRNA$^{Ala}$ gene of 73 bp. The size of the sequenced ISR fragment of *A. avenae* subsp. *citrulli* was 617 bp, (FIG. 1B, Aac, shaded). It had a GC content of 48.94%, and the same single tRNA$^{Ala}$ gene. The size of the sequenced ISR fragment of other *A. avenae* subsp. *avenae* strains was 619 bp for CAa4, 617 bp for ATCC19860, and 618 bp for MAFF301030 and MAFF301027 (FIG. 4). They had a GC content of 49.1%, 48.9%, 49.5%, and 49.5%, respectively, and a single tRNA$^{Ala}$ gene of 73 bp. The sequences were first aligned by using the DNASIS program (Hitachi SEQ, Ltd.) and the alignments were corrected manually. This ISR sequence contained a single copy of tRNA$^{Ala}$. By comparing the gene sequence of *A. avenae* subsp. *avenae* to each strain or other bacteria such as Leuconostoc oenos (Zavaleta et al. 1996. *Microbiol.* 142:2105–2114), *Streptococcus aureus* (Gurtler et al. 1995 *Microbiol.* 141:1255–1265), *Bacillus subtilis* (Loughney et al. 1982. *Nuc. Acids Res.* 10:1607–1624) and *E. coli* (Harvey et al. 1988. *J. Bacteriol.* 170:1235–1238), the primers SEQ ID NO:1 and SEQ ID NO:2 for *A. avenae* subsp. *avenae* and SEQ ID NO:3 and SEQ ID NO:4 for *A. avenae* subsp. *citrulli* were selected (FIG. 1A, FIG. 1B). From the ISR sequences, candidate primers SEQ ID NO:1 and SEQ ID NO:2 were selected using the program OLIGO (National Biosciences, Hamel, Minn.) and synthesized commercially by GIBCO BRL (Frederick, Md.).

Figure 5A:
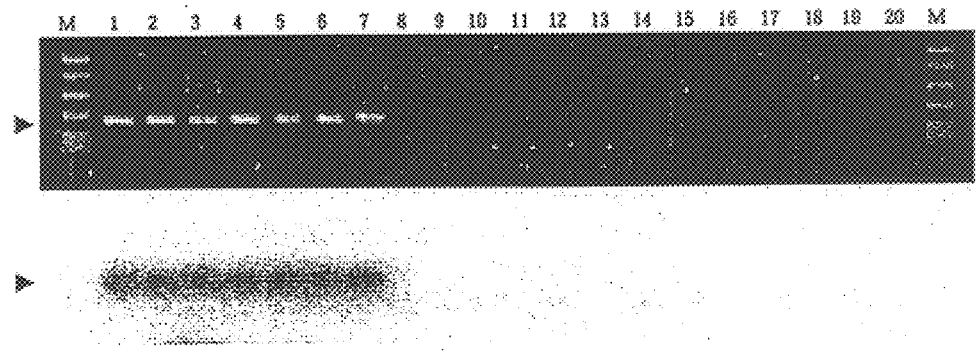
FIG. 5 illustrates the specificity of the seminested PCR assay in detecting *A. avenae* subsp. *avenae* by using lysed bacterial cultures. The amplified product of 262 bp resulting from external primers SEQ ID NO:10/SEQ ID NO:12 in the first-step PCR (FIG. 5A) and the amplified product of 242 bp resulting from nested primers SEQ ID NO:11/SEQ ID NO:12 in the seminested PCR step (FIG. 5B) were obtained from rice strains of *A. avenae* subsp. *avenae* by examination of lysed bacterial cells. The upper bands of FIG. 5A and FIG. 5B are from ethidium bromide staining and the lower bands of each are results of Southern blotting. Twenty five cycles of the first-step PCR were performed with primers SEQ ID NO:10 and SEQ ID NO:12 and a 1 μl portion of the first-step PCR product was subjected to 20 cycles of the second-step PCR with primers SEQ ID NO:11 and SEQ ID NO:12. These PCR products were separated in 1.5% agarose gels and visualized by ethidium bromide staining. Lane 1, CAa4 (rice, Korea); lane 2, ATCC19882 (rice, Japan); lane 3, MAFF301502 (rice, Japan); lane 4, 39461 g (rice, Indonesia); lane 5, Nepal (rice, Nepal); lane 6, 39123a (rice, Denmark); lane 7, Acc40560-6 (rice, Nigeria); lane 8, ATCC19860 (corn, USA); lane 9, ATCC19307 (sugarcane, Reunion); lane 10, NCPPB3111 (Canna sp., Brazil); lane 11, 3403PAv (vaseygrass, USA); lane 12, MAFF301036 (teoshinte, Japan); lane 13, 3431PAv, (millet, Nigeria); lane 14, MAFF301027 (wheatgrass, Japan); lane 15, MAFF301030 (rescuegrass, Japan); lane 16, MAFF301041 (finger millet, Japan); lane 17, CAa301cg (finger millet, Korea); lane 18, MAFF301609 (dallis grass, Japan) of *A. avenae* subsp. *avenae*; lane 19, *A. avenae* subsp. *cattleyae* ATCC33619; lane 20, *A. avenae* subsp. *citrulli* ATCC29625; and lane M, PCR-marker (GIBCO BRL, USA).
Figure 5B:
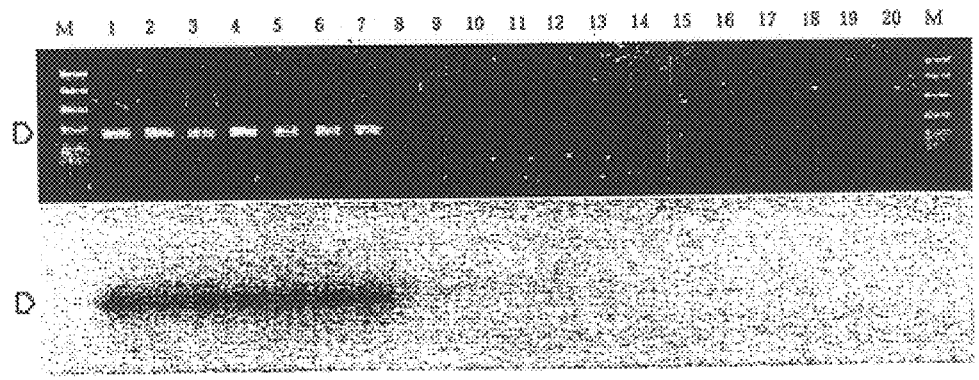

Additionally, for the rice strains of *A. avenae* subsp. *avenae*, candidate primers were also selected using the OLIGO program (supra). Oligonucleotide primers SEQ ID NOs: 10, 11, and 12 were selected from the ISR sequence of *A. avenae* subsp. *avenae* for use in the seminested PCR assay. The sequences of the selected nested primers were as follows: 5'-GTCATCCTCCACCAACCAAG-3' (SEQ ID NO:10); 5'-AGATGCCCTGCGGTAGGGCG-3' (SEQ ID NO:11); and 5'-AGAACAATTCGTCATTACTGAAC-3' (SEQ ID NO:12). External primer pair SEQ ID NO:10 and SEQ ID NO:12 amplified a fragment having a size of 262 bp for all rice strains of *A. avenae* subsp. *avenae* (FIG. 5A; Table 2). Neither the strains of *A. avenae* subsp. *avenae* from other hosts, the closely related *A. avenae* subsp. *cattleyae* and *citrulli*, or other bacteria tested, including 39 strains of Acidovorax, Burkholderia, or Xanthomonas produced a detectable PCR product using external primers. The size of the final PCR product obtained with nested primer pair SEQ ID NO:11 and SEQ ID NO:12 was 241 bp with all rice strains of *A. avenae* subsp. *avenae*. No other bacteria produced a detectable PCR product with nested PCR (FIG. 5B; Table 2). Finally, twenty nine strains of unidentified seedborne bacteria failed to generate any product with external or nested primers. All primers were synthesized commercially by Bioneer Corporation (Chungwon, Chungbuk, Korea).

Minor errors of PCR and sequencing reactions were eliminated by sequencing both strands from two independently cloned fragments of separate PCR experiments. No sequence variability between the two 16S–23S ISR copies was found.

Example 7
Polymerase Chain Reaction

Primers were screened for specificity in 25 μl reactions containing 2–5 μl of the bacterial cell suspensions, 1.5 mM MgCl$_2$, 200 μM each of dNTPs, 4 pmole of each primer, 1×PCR reaction buffer II and 1.0 U of AMPLITAQ Gold polymerase (Perkin Elmer). All amplifications were conducted in a Perkin Elmer 9600 thermocycler (Perkin Elmer Cetus, Norwalk, Conn.). For primers having SEQ ID NO:1 and SEQ ID NO:2, the amplifications were conducted with an initial DNA denaturation at 94° C. for 30 S; 55° C. for 30 S; 72° C. for 1 min and a final extension step of 7 min at 72° C. For the primers of SEQ ID NO:3 and SEQ ID NO:4, the amplifications were conducted with an initial DNA denaturation at 94° C. for 10 min followed by 5 cycles of 94° C. for 30 S; 56° C. for 30 S; 72° C. for 1 min, then 25 cycles of 94° C. for 45 S; 55° C. for 45 S; 72° C. extension step as above. For external primers (SEQ ID NO:10 and SEQ ID NO:12), the amplifications were conducted with an initial DNA denaturation at 94° C. for 10 min followed by 25 cycles of 94° C. for 30 S; 53° C. for 30 S; 72° C. for 30S, and a final extension step as above. For nested primers (SEQ ID NO:11 and SEQ ID NO:12), the amplifications were conducted with 1 μl of external product using an initial DNA denaturation at 94° C. for 5 min followed by 3 cycles of 94° C. for 30 S; 60° C. for 30 S; 72° C. for 30S, 3 cycles of 94° C. for 30 S; 48° C. for 30 S; 72° C. for 30S, then 25 cycles of 94° C. for 30 S, 53° C. for 30 S, 72° C. for 30S and a final extension step as above. To detect a product, 5 to 10 μl of the amplicate were electrophoresed on 1.2% agarose gels and stained with ethidium bromide as described (Maniatis et al. 1989. Molecular Cloning, a Laboratory Manual. Cold Spring Harbor Laboratory, Cold Spring Harbor, N.Y.).

The primers having SEQ ID NO:1 and SEQ ID NO:2 of *A. avenae* subsp. *avenae* and SEQ ID NO:3 and SEQ ID NO:4 of *A. avenae* subsp. *citrulli* were used to amplify the ISR comprising a target sequence of DNA of 43 strains of *A. avenae*, 11 strains of *A. avenae* subsp. *citrulli*, four of *A. avenae* subsp. *cattleyae*, single strains of *A. konjaci* and *A. facilis*, 26 other known bacteria, and 27 unknown bacteria isolated from seeds. The specificity of each set of primers is illustrated in Table 1. For primers having SEQ ID NO:1 and SEQ ID NO:2, a PCR product of 550 bp was obtained for all strains of *A. avenae* subsp. *avenae* and *A. avenae* subsp. *citrulli* and the ATCC strain of *A. avenae* subsp. *cattleyae*. All three strains of *A. avenae* subsp. *cattleyae* and the single strain of *A. konjaci* were negative. All other bacteria, including 1–6 strains each of five other species of non-fluorescent pseudomonads (including 12 strains of Burkholderia), four fluorescent pseudomonads, two xanthomonads, two erwinea, and six strains of unknown bacteria from rice seed were negative. Primers having SEQ ID NO:3 and SEQ ID NO:4 produced a 450-bp product unique to all strains of *A. avenae* subsp. *citrulli*; all other bacteria tested were negative (Table 1 and FIG. 2B). The specificity of each set of primers is illustrated in Table 1. Cells of 76 strains of *A. avenae* subsp. *avenae*, 10 strains of *A. avenae* subsp. *citrulli*, two strains of *A. avenae* subsp. *cattleyae*, two strains of *A. konjaci* and a single strain of *A. facilis* (type strain of the genus), 24 strains of other known rice pathogenic bacteria, 11 strains of other outgroup species, and 29 isolates of unknown non-pathogenic bacteria from rice seeds were used to screen the primer pairs SEQ ID NOs:10 and 12 and SEQ ID NOs: 11 and 12 (Table 2).

Example 8
Sensitivity of Seminested PCR with Pure Cultures and Inoculated Seed Samples To determine the minimum number of *A. avenae* subsp. *avenae* cells that could be amplified, serial dilutions of boiled lysates containing known numbers of bacterial cells were examined. As few as 1–2 CFU of *A. avenae* subsp. *avenae* Caa4 or ATCC19882 could be detected with ethidium bromide-stained gels using external primers, only (results not shown).

A total of 20 seed samples were inoculated with *A. avenae* subsp. *avenae* Caa4 and examined with and without overnight enrichment. The results obtained for samples analyzed without enrichment were varied (Table 3). The plating method with enrichment could detect as few as 1~2 CFU per g in two samples, but yielded negative results for three other samples. The seminested PCR method detected 1–2 CFU per g after overnight enrichment of all samples (Table 3). Thus, the assay works with seeds containing high levels of background flora and low levels of *A. avenae* subsp. *avenae*. All uninoculated control samples were negative, with and without enrichment, indicating that samples were not naturally contaminated with cells of *A. avenae* subsp. *avenae*. The results obtained for seed samples analyzed at zero time without enrichment varied considerably, indicating the need for an enrichment step in order to obtain reproducible results and a high degree of sensitivity.

As shown in Table 3, there is a difference in the detection rate of *A. avenae* subsp. *avenae* in seed samples with and without enrichment and also when plating and PCR are compared. Without enrichment, 14 of 48 (29.2%) seed samples are positive by the plating method, and 26 of 48 (54.2%) are positive by the classical PCR method. However, with enrichment, positive samples increased to 25 of 48 (52.1%) by the plating method and to 38 of 48 (77.1%) by BIO-PCR. Thus, BIO-PCR with liquid enrichment increased the percentage of detection by 23% over classical PCR (54.2% to 77.1%).

Example 9
Detection of *A. avenae* subsp. *avenae* in Naturally Infected Seeds

The detection efficiency of the seminested BIO-PCR assay was compared with that of the agar plating and classical PCR methods using seed samples from naturally infected seeds. In addition, the methods were compared with and without an enrichment step.

*A. avenae* subsp. *avenae* was detected by classical PCR in 26 of 48 samples (Table 3). BIO-PCR with liquid NBY medium was even less sensitive, detecting only 18 of 48 samples. However, BIO-PCR with the newly described liquid SPL medium resulted in detection of *A. avenae* subsp. *avenae* in 37 of 48 samples (Table 3). Agar plating with or without enrichment was very insensitive. However, the detection efficiency of agar plating was equal to classical PCR (25 vs. 26) when samples were first enriched in SPL broth (Table 3). When analyzing old seed samples collected in 1993 and 1994, two of five were positive by agar plating and by BIO-PCR.

Example 10
Selection of Primers and Probes for TaqMan PCR

Primer and fluorescent probe sequences for the TaqMan PCR assay were designed with the Primer Design software program from the manufacturer (PE Applied Biosystems, Foster City, Calif.) using the sequences: SEQ ID NO:4, SEQ ID NO:5, SEQ ID NO:6. Several combinations of forward (F) and reverse (R) primer and TaqMan probe (SEQ ID NO:7) sequences were tested for their performance as determined by Cycle Threshold (Ct) values. Ct value is defined as the PCR cycle number at which the signal of the probe rises above background. The lower the Ct value, the better the PCR performance. TaqMan reactions were analyzed for 40–45 cycles using an ABI Prism 7700 Sequence detection System (PE Applied Biosystems) following methods recommended by the manufacturer. Dilutions of cells or DNA of *A. avenae* subsp. *citrulli* and water (negative control) were measured.

To determine inherent sensitivity and Ct values of TaqMan and *A. avenae* subsp. *citrulli* primers (SEQ ID NO:4, SEQ ID NO:5, and SEQ ID NO:6), a titration using 1 to 100,000 pg from four replicates of five- and ten-fold dilutions of purified genomic DNA from *A. avenae* subsp. *citrulli* was performed. Under the same PCR cycling conditions for classical and BIO-PCR, ten-fold serial dilutions of $10^{-6}$ of a liquid NBY culture of *A. avenae* subsp. *citrulli* were prepared. For classical TaqMan PCR, aliquots of 14 µl of dilutions of $10^{-3}$, $10^{-4}$, $10^{-5}$, and $10^{-6}$ were tested in duplicate. For BIO-PCR, aliquots of 100 µl of the same dilutions were plated onto 8 plates each of KB, NA, YDC, and semiselective SNR medium. After 72 hrs, four plates were washed, as described in Example 2, and four kept for determining the number of cfu's of *A. avenae* subsp. *citrulli* on KB, NA, YDC, and SNR agar media after 4 and 7 days.

Example 11
Specificity and Sensitivity of Primers

Figure 3:
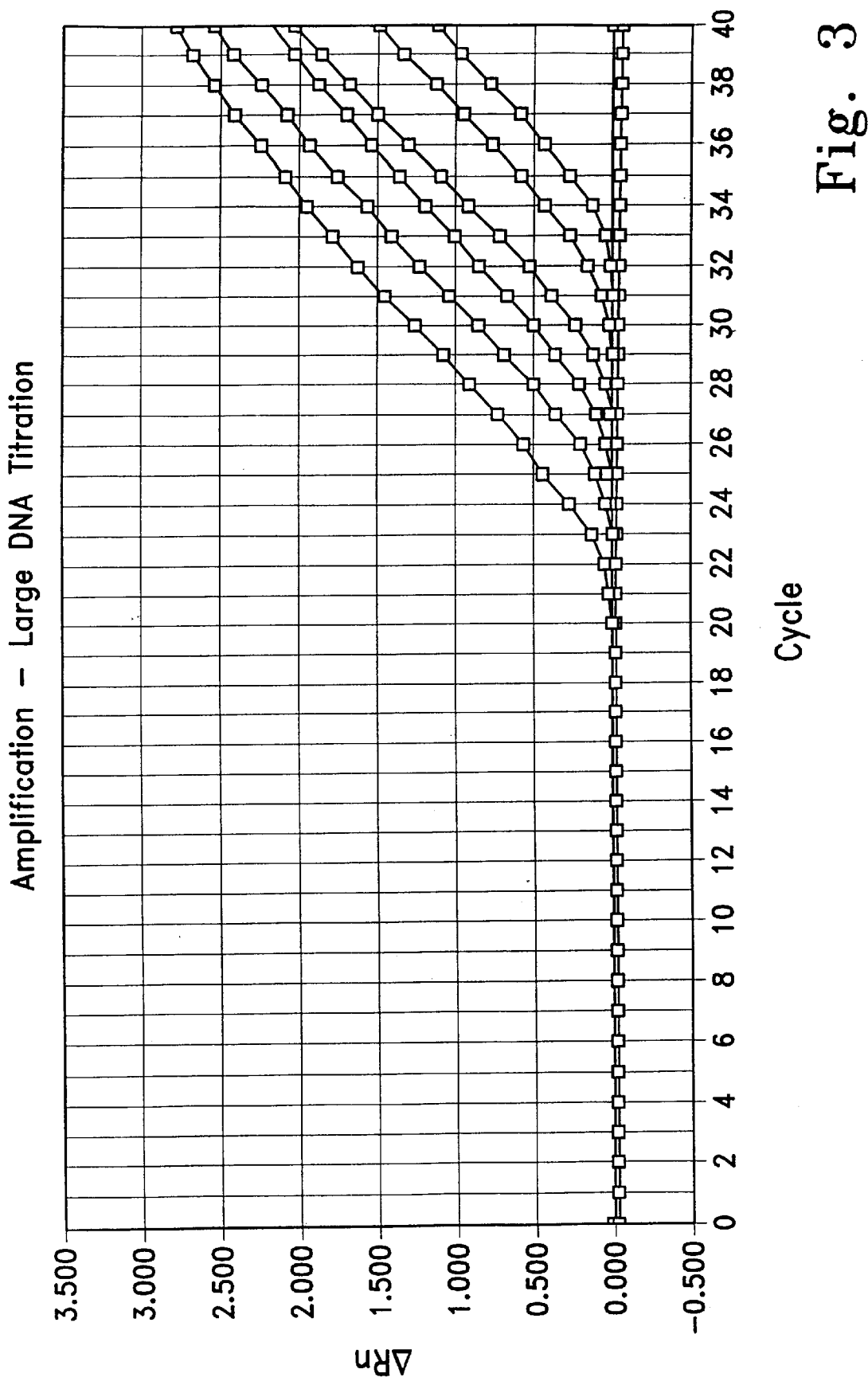
FIG. 3 shows the amplification plot from the TaqMan PCR method where the accumulation of the fluorescent signal from reporter dye molecules is monitored at each PCR cycle for dilutions of DNA from *A. avenae* subsp. *citrulli* utilizing the primers SEQ ID NO: 5 and SEQ ID NO:4 and the probe SEQ ID NO:7. The concentrations of DNA shown are left to right: E5, 1000 pg; E6, 500 pg; E7, 100 pg; E8, 50 pg; E9, 10 pg; E10, 5 pg; E11, 1 pg; and E12, water control, (baseline).

Forward primer 5'-CCTCCACCAACCAATACGCT-3' (SEQ ID NO: 5), reverse primer 5'-TCGTCATTACTGAAATTTCAACA-3' (SEQ ID NO:4), and TaqMan probe 5'-CGGTAG GGCGAAGAAACCAA-CACC (SEQ ID NO:7) resulted in a Ct value of 14.62, the lowest Ct value for 100,000 pg DNA. The next lowest Ct value, 15.40, was observed when forward primer 5'-CCTCCACCAACCAATACGCT-3' (SEQ ID NO: 5), reverse primer 5'-CATGCTCTTAGTCACTTGACCCTA-3' (SEQ ID NO:6), and TaqMan probe 5'-CGGTAG GGC-GAAGAAACCAACACC (SEQ ID NO:7) were utilized. FIG. 3 shows the best primers. All other primers had much higher Ct values (Table 4). Utilizing the best two primer sets; SEQ ID NOs: 5&4 and 5&6, the DNA titration results show that fluorescence rises above background after 33 and 37 cycles, respectively, for 1 pg DNA. FIG. 3 shows a typical titration curve for the primer set SEQ ID NOs:5 and 4. Suspensions of *A. avenae* subsp. *citrulli* containing around 10 cfu/ml were consistently positive by classical TaqMan PCR. Washings of 72-hr plates of KB, NA, YDC, and SNR media containing 1–2 colonies of *A. avenae* subsp. *citrulli* were consistently positive by TaqMan BIO-PCR.

TABLE 4

Selection of primers and probe combinations for TaqMan PCR

| Primers & Probe Set | | Whole Cell Titrations (Dilutions) | | | | | |
|---|---|---|---|---|---|---|---|
| | | Ct(-2) | Ct(-4) | Ct(-6) | Rn(-2) | Rn(-4) | Rn(-6) |
| AACF2/AACR2 | AaP1 | 28.84 | 30.30 | 40.00 | 1.05 | 0.27 | 0.00 |
| AACF2/AACR4 | AaP1 | 24.22 | 31.02 | 37.95 | 2.17 | 0.88 | 0.20 |
| SEQ ID NOs: 5, 4 | 7 | 16.27 | 23.02 | 30.98 | 3.07 | 2.50 | 1.30 |
| SEQ ID NOs: 5, 6 | 7 | 17.79 | 22.81 | 32.39 | 3.13 | 2.21 | 0.71 |

| Primers & Probe Set | | DNA Titration (Ct Values) | | | | | | | |
|---|---|---|---|---|---|---|---|---|---|
| | | 100,000 | 50,000 | 10,000 | 1,000 | 100 | 10 | 1 | 0 |
| AACF2/AACR4 | AaP1 | 20.78 | 21.20 | 23.15 | 26.87 | 31.54 | 36.99 | 37.83 | 40 |
| SEQ ID NOs: 5, 4 | 7 | 14.62 | 14.93 | 16.95 | 20.58 | 25.18 | 28.82 | 33.83 | 40 |
| SEQ ID NOs: 5, 6 | 7 | 15.40 | 15.81 | 18.06 | 22.43 | 27.40 | 31.75 | 37.62 | 40 |

The forward primer 5'-CCTCCACCAACCAATACGCT-3' (SEQ ID NO: 5) and the reverse primer of 5'-TCGTCATTACTGAATTTCIMCA-3' (SEQ ID NO: 4) of *A. avenae* subsp. *citrulli* were used to amplify the ISR of 16 strains of *A. avenae* subsp. *avenae*, 11 strains of *A. avenae* subsp. *citrulli*, a single strain of *A. facilis*, 18 strains of pseudomonads, four xanthomonads, and two flavobacteria. For these primers, an amplified fluorescent signal was obtained with all strains of *A. avenae* subsp. *citrulli* specifically; all other bacteria were negative, as illustrated in Table 5.

TABLE 5

Species and strains and results of PCR with primers SEQ ID NOS: 5 & 4 of *A. avenae* subsp. *citrulli*

| Organism | Origin | PCR Amplification SEQ ID NOS: 5 & 4[a] |
|---|---|---|
| *A. avenae* subsp. *avenae* | | |
| Fc 158 (ATCC 40582 E1) | Mortensen, Denmark | – |
| Fc 159 (ATCC 40580) | Mortensen, Denmark | – |
| Fc 160 (391226) | Mortensen, Denmark | – |
| Fc 172 (ATCC 40582 A1) | Mortensen, Denmark | – |
| Fc 189 (301507) | Takikawa, Japan | – |
| Fc 190 (301508) | Takikawa, Japan | – |
| Fc 191 (301511) | Takikawa, Japan | – |
| Fc 192 (311058) | Takikawa, Japan | – |
| Fc 193 (301509) | Takikawa, Japan | – |
| Fc 194 (301510) | Takikawa, Japan | – |

TABLE 5-continued

Species and strains and results of PCR with primers SEQ ID NOS: 5 & 4 of *A. avenae* subsp. *citrulli*

| Organism | Origin | PCR Amplification SEQ ID NOS: 5 & 4[a] |
|---|---|---|
| Fc 195 (311057) | Takikawa, Japan | – |
| Fc 196 (311056) | Takikawa, Japan | – |
| Fc 197 (301506) | Takikawa, Japan | – |
| Fc 198 (301504) | Takikawa, Japan | – |
| Fc 199 (301503) | Takikawa, Japan | – |

TABLE 5-continued

Species and strains and results of PCR with primers SEQ ID NOS: 5 & 4 of *A. avenae* subsp. *citrulli*

| Organism | Origin | PCR Amplification SEQ ID NOS: 5 & 4[a] |
|---|---|---|
| Fc 200 (301502) | Takikawa, Japan | – |
| *A. avenae* subsp. *citrulli* | | |
| Fc 141 (Aac-H1B) | Randhawa, Seed | + |
| Fc 181 (Aac H17) | Randhawa, Seed | + |
| Fc 201 (8408) | R. Latin, Purdue | + |
| Fc 203 (Aac 2576) | Randhawa, Seed | + |
| Fc 204 (Aac 2578) | Randhawa, Seed | + |
| Fc 247 (ATCC 29625) | Schaad, Georgia | + |
| Fc 248 (Aac 206) | Randhawa, Seed | + |
| Fc 249 (isa 3) | Randhawa, Seed | + |
| Fc 250 (isa 4) | Randhawa, Seed | + |
| Fc 251 (isa 5) | Randhawa, Seed | + |
| Fc 253 (isa 12) | Randhawa, Seed | + |
| *A. facilis* | | |
| Fc 208 (ATCC 6230) | | – |
| *Pseudomonas pseudoalcaligenes* subsp. *pseudoalcaligenes* | | |
| Fc 206 (ATCC 26550) | | – |
| *P. aptata* | | |
| Fc 218 (8545) | Gvozdyak, Ukraine | – |

TABLE 5-continued

Species and strains and results of PCR with primers SEQ ID NOS: 5 & 4 of *A. avenae* subsp. *citrulli*

| Organism | Origin | PCR Amplification SEQ ID NOS: 5 & 4[a] |
|---|---|---|
| *P. wieringae* | | |
| Fc 219 (7921) | Gvozdyak, Ukraine | − |
| Fc 220 (7923) | Gvozdyak, Ukraine | − |
| *P. panici* | | |
| Fc 221 (7963) | Gvozdyak, Ukraine | − |
| Fc 222 (7963*) | Gvozdyak, Ukraine | − |
| *P. xanthochlora* | | |
| Fc 223 (8538) | Gvozdyak, Ukraine | − |
| Fc 224 (8540) | Gvozdyak, Ukraine | − |
| *P. lupini* | | |
| Fc 225 (8532) | Gvozdyak, Ukraine | − |
| Fc 226 (8533) | Gvozdyak, Ukraine | − |
| *P. solancearum* | | |
| Fc 228 (AW1) | Denny, Georgia | − |
| Fc 229 (AW1-PC) | Denny, Georgia | − |
| *P. rubrisubalbicans* | | |
| Fc 97 (PR108) | Buddenhagen, Hawaii | − |
| Fc 98 (PR110) | Hayward, Hawaii | − |
| *P. syringae* pv. *syringae* | | |
| Fc 103 (301D) | Hutchenson, Maryland | − |
| Fc 108 (B 728a) | Gross, Washington | − |
| *P. fluorescens* | | |
| Fc 117 (4SI-14) | Kloepper, Alabama | − |
| Fc 118 (4SI-15) | Kloepper, Alabama | − |

TABLE 5-continued

Species and strains and results of PCR with primers SEQ ID NOS: 5 & 4 of *A. avenae* subsp. *citrulli*

| Organism | Origin | PCR Amplification SEQ ID NOS: 5 & 4[a] |
|---|---|---|
| *Xanthomonas albilineans* | | |
| Fb 581 (Xa 15009) | Rott, Guadeloupe | − |
| Fb 582 (Xa 150010) | Rott, Madagascar | − |
| Fb 616 (Xa 93–170) | Comstock, Florida | − |
| *X. cucurbitae* | | |
| Fb 1054 | Schaad, Maryland | − |
| *Flavobacterium balustinum* | | |
| Fb 1081 (ATCC 53198) | Hoitink, Ohio | − |
| *Flavobacterium sp.* | | |
| Fb 1082 (ATCC 39723) | Crawford, Idaho | − |

[a]Positive result means presence of an amplified fluorescent signal from the reporter dye molecule and negative means no fluorescent signal.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An oligonucleotide primer comprising the sequence 5'-GTCATCCTCCACCAACC AAG-3' (SEQ ID NO:10) or a portion of SEQ ID NO: 10, wherein the primer is eighteen to twenty-four nucleotides in length, comprises at least one unique nucleotide as identified in FIG. 4 as a mismatch between strains of *Acidovorax avenae* subsp. *avenae* from rice and those of corn, rescue grass, or wheat grass, specifically hybridizes to a region of SEQ ID NO:13 or its complement, and distinguishes rice strains of *Acidovorax avenae* subsp. *avenae* (1) from other strains of *Acidovorax avenae* subsp. *avenae* isolated from plants other than rice and (2) from other subspecies of *A. avenae.*

2. An oligonucleotide primer comprising the sequence 5'-AGAACAATTCGTCATTAC TGAAC-3' (SEQ ID NO:12) or a portion of SEQ ID NO: 12, wherein the primer is eighteen to twenty-four nucleotides in length, comprises at least one unique nucleotide as identified in FIG. 4 as a mismatch between strains of *Acidovorax avenae* subsp. *avenae* from rice and those of corn, rescue grass, or wheat grass, specifically hybridizes to a region of SEQ ID NO:13 or its complement, and distinguishes rice strains of *Acidovorax avenae* subsp. *avenae* (1) from other strains of *Acidovorax avenae* subsp. *avenae* isolated from plants other than rice and (2) from other subspecies of *A. avenae.*

3. A primer set comprising oligonucleotides comprising the sequence 5'-GTCATCCTC CACCAACCAAG-3' (SEQ ID NO:10) and the sequence 5'-AGAACAATTCGTCATTACT GAAC-3' (SEQ ID NO:12) or portions of SEQ ID NO: 10 and SEQ ID NO:12, wherein the primer set comprises primers eighteen to twenty-four nucleotides in length and at least one unique nucleotide as identified in FIG. 4 as a mismatch between strains of *Acidovorax avenae* subsp. *avenae* from rice and those of corn, rescue grass, or wheat grass, specifically hybridizes to a region of SEQ ID NO:13 or its complement, and distinguishes rice strains of *Acidovorax avenae* subsp. *avenae* (1) from other strains of *Acidovorax avenae* subsp. *avenae* isolated from plants other than rice and (2) from other subspecies of *A. avenae.*

4. An oligonucleotide primer comprising the sequence 5'-AGATGCCCTGCGGTAGG GCG-3' (SEQ ID NO:11) or a portion of SEQ ID NO: 11, wherein the primer is eighteen to twenty-four nucleotides in length, comprises at least one unique nucleotide as identified in FIG. 4 as a mismatch between strains of *Acidovorax avenae* subsp. *avenae* from rice and those of corn, rescue grass, or wheat grass, specifically hybridizes to a region of SEQ ID NO:13 or its complement, and distinguishes rice strains of *Acidovorax avenae* subsp. *avenae* (1) from other strains of *Acidovorax avenae* subsp. *avenae* isolated from plants other than rice and (2) from other subspecies of *A. avenae.*

5. A primer set comprising oligonucleotides comprising the sequence 5'-AGATGCCC TGCGGTAGGGCG-3' (SEQ ID NO:11) and the sequence 5'-AGAACAATTCGTCATTA CTGAAC-3' (SEQ ID NO:12) or portions of SEQ ID NO: 11 and SEQ ID NO:12, wherein the primer set comprises primers eighteen to twenty-four nucleotides in length and at least one unique nucleotide as identified in FIG. 4 as a mismatch between strains of *Acidovorax avenae* subsp. *avenae* from rice and those of corn, rescue grass, or wheat grass, specifically hybridizes to a region of SEQ ID NO:13 or its complement, and distinguishes rice strains of *Acidovorax avenae* subsp. *avenae* (1) from other strains of *Acidovorax avenae* subsp. *avenae* isolated from plants other than rice and (2) from other subspecies of *A. avenae.*

6. An oligonucleotide primer comprising the sequence 5'-AATTTTTGTTGCCGACGG CACG-3' (SEQ ID NO:16) or a portion of SEQ ID NO:16, wherein the primer is eighteen to twenty-four nucleotides in length, comprises at least one unique nucleotide as identified in FIG. 4 as a mismatch between strains of *Acidovorax avenae* subsp. *avenae* from rice and those of corn, rescue grass, or wheat grass, specifically hybridizes to a region of SEQ ID NO:13 or its complement, and distinguishes rice strains of *Acidovorax avenae* subsp. *avenae* (1) from other strains of *Acidovorax avenae* subsp. *avenae* isolated from plants other than rice and (2) from other subspecies of *A. avenae.*

7. An intergenic spacer region (ISR) sequence selected from the group consisting of: ISR1 of rice strains of *Acidovorax avenae* subsp. *avenae* comprising the nucleotides of SEQ ID NO:13, ISR2 of corn strains of *A. avenae* subsp. *avenae* comprising the nucleotides of SEQ ID NO:14, ISR3 of rescue grass strains of *A. avenae* subsp. *avenae* comprising the nucleotides of SEQ ID NO:15, and ISR4 of wheat grass strains of *A. avenae* subsp. *avenae* comprising the nucleotides of SEQ ID NO:15.

8. An oligonucleotide primer comprising a portion of SEQ ID NO: 13 or its complement, wherein said primer is eighteen to twenty-four nucleotides in length, comprises at least one unique nucleotide as identified in FIG. 4 as a mismatch between strains of *Acidovorax avenae* subsp. *avenae* from rice (SEQ ID NO:13) and those of corn (SEQ ID NO:14) or rescue or wheat grasses (SEQ ID NO:15), specifically hybridizes to a region of SEQ ID NO:13 or its complement, and distinguishes rice strains of *Acidovorax avenae* subsp. *avenae* (1) from other strains of *Acidovorax avenae* subsp. *avenae* isolated from plants other than rice and (2) from other subspecies of *A. avenae.*

9. A method of detecting the presence of rice strains of *Acidovorax avenae* subsp. *avenae* by polymerase chain reaction, said method comprising:

a) providing DNA of said rice strains of *A. avenae* subsp. *avenae* or a test sample of cells or microorganisms suspected of containing DNA of said rice strains of *A. avenae* subsp. *avenae* ;

b) amplifying a target sequence of DNA of said Acidovorax using at least one primer selected from the group consisting of an oligonucleotide primer comprising the sequence 5'-GTCATCCTCCACCAACCAAG-3' (SEQ ID NO:10), the sequence 5'-AGATGCCCTGCGGTAGGGCG-3' (SEQ ID NO:11), the sequence 5'-AGAACAATTCGTCATTACTGAAC-3' (SEQ ID NO:12), a portion of SEQ ID NO:10, a portion of SEQ ID NO: 11, and a portion of SEQ ID NO:12, wherein the primer is eighteen to twenty-four nucleotides in length, comprises at least one unique nucleotide as identified in FIG. 4 as a mismatch between strains of *Acidovorax avenae* subsp. *avenae* from rice and those of corn, rescue grass, or wheat grass, specifically hybridizes to a region of SEQ ID NO:13 or its complement, and distinguishes rice strains of *Acidovorax avenae* subsp. *avenae* (1) from other strains of *Acidovorax avenae* subsp. *avenae* isolated from plants other than rice and (2) from other subspecies of *A. avenae*; and c) detecting the presence of the amplification products of the target sequence of DNA as an indication of the presence of rice strains of *A. avenae* subsp. *avenae* .

10. A method of detecting the presence of rice strains of *Acidovorax avenae* subsp. *avenae* by polymerase chain reaction, said method comprising:

a) providing DNA of said rice strains of *A. avenae* subsp. *avenae* or a test sample of cells or microorganisms suspected of containing DNA of said rice strains of *A. avenae* subsp. *avenae* ;

b) amplifying a target sequence of DNA of said rice strains of *A. avenae* subsp. *avenae* using a primer set comprising oligonucleotides comprising the sequence 5'-GTCATCCTCCACCAACCAAG-3' (SEQ ID NO:10) and the sequence 5'-AGAACAATTCGTCATTACTGAAC-3' (SEQ ID NO:12) or portions of SEQ ID NO: 10 and SEQ ID NO:12, wherein the primer set comprises primers eighteen to twenty-four nucleotides in length and at least one unique nucleotide as identified in FIG. 4 as a mismatch between strains of *Acidovorax avenae* subsp. *avenae* from rice and those of corn, rescue grass, or wheat grass, specifically hybridizes to a region of SEQ ID NO: 13 or its complement, and distinguishes rice strains of *Acidovorax avenae* subsp. *avenae* (1) from other strains of *Acidovorax avenae* subsp. *avenae* isolated from plants other than rice and (2) from other subspecies of *A. avenae*; and c) detecting the presence of the amplification products of the target sequence of DNA as an indication of the presence of rice strains of *A. avenae* subsp. *avenae* .

11. A method of detecting the presence of rice strains of *Acidovorax avenae* subsp. *avenae* by polymerase chain reaction, said method comprising:

a) providing DNA of said rice strains of *A. avenae* subsp. *avenae* or a test sample of cells or microorganisms suspected of containing DNA of said rice strains of *A. avenae* subsp. *avenae* ;

b) amplifying a target sequence of DNA of said rice strains of *A. avenae* subsp. *avenae* using a primer set comprising oligonucleotides comprising the sequence 5'-AGATGCCCTGCGGTAGGGCG-3' (SEQ ID NO:11) and the sequence 5'-AGAACAATTCGTCATTACTGAAC-3' (SEQ ID NO:12) or at least those portions of SEQ ID NO: 11 and SEQ ID NO:12, wherein the primer set comprises primers eighteen to twenty-four nucleotides in length and at least one unique nucleotide as identified in FIG. 4 as a mismatch between strains of *Acidovorax avenae* subsp. *avenae* from rice and those of corn, rescue grass, or wheat grass, specifically hybridizes to a region of SEQ ID NO:13 or its complement, and distinguishes rice strains of *Acidovorax avenae* subsp. *avenae* (1) from other strains of *Acidovorax avenae* subsp. *avenae* isolated from plants other than rice and (2) from other subspecies of *A. avenae*; and c) detecting the presence of the amplification products of the target sequence of DNA as an indication of the presence of rice strains of *A. avenae* subsp. *avenae* .

12. A method of detecting the presence of rice strains of *Acidovorax avenae* subsp. *avenae* by polymerase chain reaction, said method comprising:

a) providing DNA of said rice strains of *A. avenae* subsp. *avenae* or a test sample of cells or microorganisms suspected of containing DNA of said rice strains of *A. avenae* subsp. *avenae* ;

b) amplifying a target sequence of DNA of said rice strains of *A. avenae* subsp. *avenae* using a primer set comprising external primers comprising the sequence 5'-GTCATCCTCCACCAACCAAG-3' (SEQ ID NO:10) and the sequence 5'-AGAACAATTCGTCATTACTGAAC-3' (SEQ ID NO:12) or portions of SEQ ID NO: 10 and SEQ ID NO:12, wherein the primer set comprises primers eighteen to twenty-four nucleotides in length and at least one unique nucleotide as identified in FIG. 4 as a mismatch between strains of *Acidovorax avenae* subsp. *avenae* from rice and those of corn, rescue grass, or wheat grass, specifically hybridizes to a region of SEQ ID NO:13 or its complement, and distinguishes rice strains of *Acidovorax avenae* subsp. *avenae* (1) from other strains of *Acidovorax avenae* subsp. *avenae* isolated from plants other than rice and (2) from other subspecies of *A. avenae;* c) detecting the presence of the external amplification products of the target sequence of DNA as an indication of the presence of rice strains of *A. avenae* subsp. *avenae* ;

d) amplifying the resulting external amplification products of the target sequence of DNA using a primer set comprising nested primers comprising the sequence 5'-AGATGCCCTGCGGTAGGGCG-3' (SEQ ID NO: 11) and the sequence 5'-AGAACAATTCGTCATTACTGAAC-3' (SEQ ID NO:12) or portions of SEQ ID NO: 11 and SEQ ID NO:12, wherein the primer set comprises primers eighteen to twenty-four nucleotides in length and at least one unique nucleotide as identified in FIG. 4 as a mismatch between strains of *Acidovorax avenae* subsp. *avenae* from rice and those of corn, rescue grass, or wheat grass, specifically hybridizes to a region of SEQ ID NO:13 or its complement, and distinguishes rice strains of *Acidovorax avenae* subsp. avenae (1) from other strains of *Acidovorax avenae* subsp. *avenae* isolated from plants other than rice and (2) from other subspecies of *A. avenae*; and e) detecting the presence of the nested amplification products of the target sequence of DNA as a confirmation of the presence of rice strains of *A. avenae* subsp. *avenae* .

13. The method of claim 9, 10, 11, or 12 wherein the test sample consists essentially of viable cells or microorganisms or DNA extracted from said viable cells or microorganisms; wherein said test sample results from (a) culturing said viable cells or microorganisms on agar plates or in liquid media in order to expand the number of said viable cells or microorganisms, (b) collecting the viable cells or microorganisms enriched by culturing, by either washing the plates of plated samples or collecting aliquots from liquid culture, and (c) washing the viable cells or microorganisms by filtration, centrifugation, or other conventional means.

14. The method of claim 13 wherein the medium is SPL agar or SPL liquid medium.

15. A method of evaluating or monitoring the efficacy of treatments utilized to eradicate pathogenic rice strains of *Acidovorax avenae* subsp. *avenae* from a seed lot, said method comprising:
   a) providing DNA of said rice strains of *A. avenae* subsp. *avenae* or a test sample of cells or microorganisms suspected of containing DNA of said rice strains of *A. avenae* subsp. *avenae* according to the method of any one of claims 9–11;
   b) amplifying a target sequence of DNA of said rice strains of *A. avenae* subsp. *avenae* according to the method of any one of claims 9–11;
   c) detecting the presence of the amplification products of the target sequence of DNA as an indication of the presence of rice strains of *A. avenae* subsp. *avenae* according to the method of any one of claims 9, 10, or 11;
   d) treating the seed lot from which the first test sample is obtained, or a test portion of said seed lot, with a composition to reduce or eradicate rice strains of *A. avenae* subsp. *avenae* ;
   e) providing a second test sample from the substance undergoing treatment to reduce or eradicate rice strains of *A. avenae* subsp. *avenae* ;
   f) amplifying a target sequence of DNA of said rice strains of *A. avenae* subsp. *avenae* utilizing the particular primer or primer sets of step b to provide DNA amplification products of said rice strains of *A. avenae* subsp. ;
   g) detecting the amount of the amplification products of the target sequence of DNA in said second test sample; and
   h) comparing the amount of amplification products or absence of amplification products in the second test sample to the amount of amplification products detected in the first test sample in step (c), as an indication of whether or not the treatment protocol has been successful in reducing or eradicating rice strains of *A. avenae* subsp. *avenae* .

16. A method of evaluating or monitoring the efficacy of treatments utilized to eradicate pathogenic rice strains of *A. avenae* subsp. *avenae* from a seed lot, said method comprising:
   a) steps a–e of claim 12;
   b) treating the seed lot from which the first test sample is obtained, or a test portion of said seed lot, with a composition to reduce or eradicate rice strains of *A. avenae* subsp. *avenae* ;
   c) providing a second test sample from the substance undergoing treatment to reduce or eradicate rice strains of *A. avenae* subsp. *avenae* ;
   d) repeating steps a–e of claim 12; and
   e) comparing the amount of nested amplification products or absence of nested amplification products in the second test sample to the amount of nested amplification products detected in the first test sample, as an indication of whether or not the treatment protocol has been successful in reducing or eradicating rice strains of *A. avenae* subsp. *avenae* .

17. A kit for identifying rice strains of *Acidovorax avenae* subsp. *avenae*, comprising at least one primer comprising the sequence 5'-GTCATCCTCCACCAACCAAG-3' (SEQ ID NO:10) or a portion of SEQ ID NO:10, wherein the primer is eighteen to twenty-four nucleotides in length, comprises at least one unique nucleotide as identified in FIG. 4 as a mismatch between strains of *Acidovorax avenae* subsp. *avenae* from rice and those of corn, rescue grass, or wheat grass, specifically hybridizes to a region of SEQ ID NO:13 or its complement, and distinguishes rice strains of *Acidovorax avenae* subsp. *avenae* (1) from other strains of *Acidovorax avenae* subsp. *avenae* isolated from plants other than rice and (2) from other subspecies of *A. avenae*.

18. A kit for identifying rice strains of *Acidovorax avenae* subsp. *avenae*, comprising at least one primer comprising the sequence 5'-AGATGCCCTGCGGTAGGGCG-3' (SEQ ID NO:11) or a portion of SEQ ID NO:11, wherein the primer is eighteen to twenty-four nucleotides in length, comprises at least one unique nucleotide as identified in FIG. 4 as a mismatch between strains of *Acidovorax avenae* subsp. *avenae* from rice and those of corn, rescue grass, or wheat grass, specifically hybridizes to a region of SEQ ID NO:13 or its complement, and distinguishes rice strains of *Acidovorax avenae* subsp. *avenae* (1) from other strains of *Acidovorax avenae* subsp. *avenae* isolated from plants other than rice and (2) from other subspecies of *A. avenae*.

19. A kit for identifying rice strains of *Acidovorax avenae* subsp. *avenae*, comprising at least one primer comprising the sequence 5'-AGAACAATTCGTCATTACTGAAC-3' (SEQ ID NO:12) or a portion of SEQ ID NO: 12, wherein the primer is eighteen to twenty-four nucleotides in length, comprises at least one unique nucleotide as identified in FIG. 4 as a mismatch between strains of *Acidovorax avenae* subsp. *avenae* from rice and those of corn, rescue grass, or wheat grass, specifically hybridizes to a region of SEQ ID NO:13 or its complement, and distinguishes rice strains of *Acidovorax avenae* subsp. *avenae* (1) from other strains of *Acidovorax avenae* subsp. *avenae* isolated from plants other than rice and (2) from other subspecies of *A. avenae*.

\* \* \* \* \*